US009252421B1

(12) United States Patent
Erickson et al.

(10) Patent No.: US 9,252,421 B1
(45) Date of Patent: Feb. 2, 2016

(54) SURFACE MODIFICATION OF ACTIVE MATERIAL STRUCTURES IN BATTERY ELECTRODES

(71) Applicant: A123 Systems LLC, Waltham, MA (US)

(72) Inventors: Michael Erickson, Plano, TX (US); Konstantin Tikhonov, Pleasanton, CA (US)

(73) Assignee: A123 Systems LLC, Waltham, MA (US)

( * ) Notice: Subject to any disclaimer, the term of this patent is extended or adjusted under 35 U.S.C. 154(b) by 0 days.

(21) Appl. No.: 14/057,931

(22) Filed: Oct. 18, 2013

(51) Int. Cl.
*B05D 5/12* (2006.01)
*H01M 4/04* (2006.01)
*H01M 4/485* (2010.01)
*H01M 4/02* (2006.01)
*H01M 4/139* (2010.01)

(52) U.S. Cl.
CPC .......... *H01M 4/0492* (2013.01); *H01M 4/0404* (2013.01); *H01M 4/485* (2013.01); *B05D 5/12* (2013.01); *H01M 4/139* (2013.01); *H01M 2004/027* (2013.01)

(58) Field of Classification Search
USPC .................. 427/115, 212, 216, 220; 429/212
See application file for complete search history.

(56) References Cited

U.S. PATENT DOCUMENTS

2006/0286444 A1* 12/2006 Nishino et al. ............... 429/120
2008/0113266 A1* 5/2008 Park et al. ..................... 429/215
2011/0091771 A1* 4/2011 Sannan et al. ................ 429/217
2011/0274982 A1* 11/2011 Kaneko et al. ................ 429/303
2013/0040193 A1* 2/2013 Tsuchida et al. .............. 429/209
2013/0149587 A1* 6/2013 Yu et al. ........................ 429/144
2013/0224608 A1* 8/2013 Sasaki et al. .................. 429/341
2013/0232772 A1 9/2013 Tikhonov et al.
2013/0244080 A1* 9/2013 Song et al. .................... 429/144
2013/0302680 A1* 11/2013 Lim et al. ...................... 429/213

FOREIGN PATENT DOCUMENTS

JP 08111243 A * 4/1996

OTHER PUBLICATIONS

"Silane Coupling Agents: Connecting Across Boundaries", Gelast, Inc., 2006, Retrieved from the Internet: <http://www.gelest.com/goods/pdf/couplingagents.pdf>, Accesed on Sep. 17, 2013, 60 pgs.

(Continued)

*Primary Examiner* — Brian K Talbot
(74) *Attorney, Agent, or Firm* — Alleman Hall McCoy Russell & Tuttle LLP

(57) ABSTRACT

Provided herein are methods of processing electrode active material structures for use in electrochemical cells or, more specifically, methods of forming surface layers on these structures. The structures are combined with a liquid to form a mixture. The mixture includes a surface reagent that chemically reacts and forms a surface layer covalently bound to the structures. The surface reagent may be a part of the initial liquid or added to the mixture after the liquid is combined with the structures. In some embodiments, the mixture may be processed to form a powder containing the structures with the surface layer thereon. Alternatively, the mixture may be deposited onto a current collecting substrate and dried to form an electrode layer. Furthermore, the liquid may be an electrolyte containing the surface reagent and a salt. The liquid soaks the previously arranged electrodes in order to contact the structures with the surface reagent.

16 Claims, 8 Drawing Sheets

(56) References Cited

OTHER PUBLICATIONS

Qin, Yan et al., "Mechanism of LTO Gassing and potential solutions", Argonne National Laboratory, May 9-13, 2011, Retrieved from the Internet: <http://www1.eere.energy.gov/vehiclesandfuels/pdfs/merit_review_2011/electrochemical_storage/es112_amine_2011_p.pdf>, Accessed on Sep. 16, 2013, 18 pgs.

* cited by examiner

SURFACE MODIFICATION OF ACTIVE MATERIAL STRUCTURES IN BATTERY ELECTRODES

GOVERNMENT RIGHTS

This invention was made with government support under DE-FC26-05NT42403 awarded by the Department of Energy. The government has certain rights in the invention.

BACKGROUND

Some surface activity of active materials used in positive and negative electrodes of electrochemical cells, such as lithium batteries, can have deleterious effects. For example, electrolytes may decompose on a surface of the negative electrode and/or positive electrode. This decomposition may be due to the catalytic activity of the electrode active material surface, electrical potential at this surface, and/or a presence of specific functional groups (e.g., hydroxyl and oxygen groups). This electrolyte decomposition and other undesirable electrode surface reactions may result in a high resistance causing capacity fade, poor rate performance, and other characteristics. Furthermore, substantial gas generation may occur inside a sealed case and cause swelling and potentially unsafe conditions. Many positive electrode materials and negative electrode materials can exhibit such deleterious activity. Nickel containing materials and titanium containing materials, such as lithium titanium oxide (LTO), are particularly prone to gas generation when used with many different electrolytes.

SUMMARY

Provided herein are methods of processing electrode active material structures for use in electrochemical cells or, more specifically, methods of forming surface layers on these structures. The structures are combined with a liquid to form a mixture. The mixture includes a surface reagent that chemically reacts and forms a surface layer covalently bound to the structures. The surface reagent may be a part of the initial liquid or added to the mixture after the liquid is combined with the structures. In some embodiments, the mixture may be processed to form a powder containing the structures with the surface layer thereon. Alternatively, the mixture may be deposited onto a current collecting substrate and dried to form an electrode layer. Furthermore, the liquid may be an electrolyte containing the surface reagent and a salt. The liquid soaks previously arranged electrodes in order to contact the structures with the surface reagent.

In some embodiments, a method of forming a surface layer on electrode active material structures for use in a lithium ion battery involves receiving the electrode active material structures and combining the electrode active material structures with a liquid to form a mixture. The mixture includes a surface reagent. The surface reagent forms the surface layer covalently bound to the electrode active material structures. The surface layer reduces reactivity of the electrode active material structures with respect to electrolyte components. In some embodiments, the electrode active material structures chemically react with the surface reagent, thereby forming the surface layer covalently bound to the electrode active material structures. Alternatively, the electrode active material structures may catalyze a chemical reaction involving the surface reagent such that the chemical reaction forms the surface layer covalently bound to the electrode active material structures.

In some embodiments, the mixture including the surface reagent is a slurry configured for coating onto a current collecting substrate. The mixture may also include a polymer binder, such as polyacrylonitrile, poly(methylmethacrylate), poly(vinyl chloride), polyvinylidene fluoride, poly(vinylidene fluoride-co-hexafluoropropene, polyacrylic acid, styrene butadiene rubber, carboxymethylcellulose, and copolymers thereof. In some embodiments, the method also involves coating the slurry onto the current collecting substrate and drying the slurry, thereby forming an electrode active material layer on the current collecting substrate.

In some embodiments, the surface reagent comprises an oxy-silane. For example, the surface reagent may include a trioxy-silane having a general formula of $R-Si(OR')_3$, such that R is one of $(CH_2)_X CH_3$, $CH=CH_2$, $(CH_2)_X(CF_2)_Y CF_3$, $(CH_2)_X Si(OCH_3)_3$, $(CH_2)_X(N_2C_3H_5)$, or $(CH_2)_X PO_3$, and X is from 0 to 15 and wherein Y is from 0 to 5. In some embodiments, R' is $(CH_2)_Z CH_3$, and Z is from 0 to 1. The surface reagent may be one of methyltrimethoxysilane or tridecafluorooctyltriethoxysilane. In some embodiments, the electrode active material includes a metal, such as titanium and/or nickel. For example, the electrode active material may be lithium titanium oxide. The amount of the surface reagent may be between about 0.25% by weight and about 5% by weight relative to the electrode active material. The formed surface layer may include siloxane.

In some embodiments, the method also involves forming a powder from the mixture. The powder may include the electrode active material having the surface layer. In some embodiments, the method involves combining the powder including the electrode active material having the surface layer with a polymer binder, thereby forming a slurry. The method then proceeds with coating the slurry onto a current collecting substrate.

In some embodiments, the mixture is operable as an electrolyte. The mixture includes an electrolyte salt in addition to the surface reagent. In some embodiments, the mixture includes water. The water catalyzes formation of the surface layer. In some embodiments, the method also involves outgassing the mixture including the electrode active material structures and the surface reagent. The method may involve heating the mixture to a temperature of at least about 80° C.

In some embodiments, a method of forming a surface layer on electrode active material structures for use in a lithium ion battery involves receiving the electrode active material structures. The electrode active material structures may include lithium titanium oxide. The method proceeds with combining the electrode active material structures with a liquid to form a slurry and adding a surface reagent into the slurry. The surface reagent may include methyltrimethoxysilane. The method proceeds with coating the slurry onto a current collecting substrate and drying the slurry on the surface of the current collecting substrate thereby forming an electrode active material layer. The electrode active material structures in the electrode active material layer may include a surface layer covalently bound to the electrode active material structures. The surface layer is formed from the surface reagent. The surface layer reduces reactivity of the electrode active material structures with respect to electrolyte components.

In some embodiments, a treated electrode active material structure includes an electrode active material structure including a metal, such as titanium and/or nickel. The treated electrode active material structure also includes a surface layer covalently bound to the electrode active material structure. The surface layer includes siloxane. The surface layer reduces reactivity of the electrode active material structure with respect to electrolyte components.

These and other embodiments are described further below with reference to the figures.

DETAILED DESCRIPTION

Figure 1:
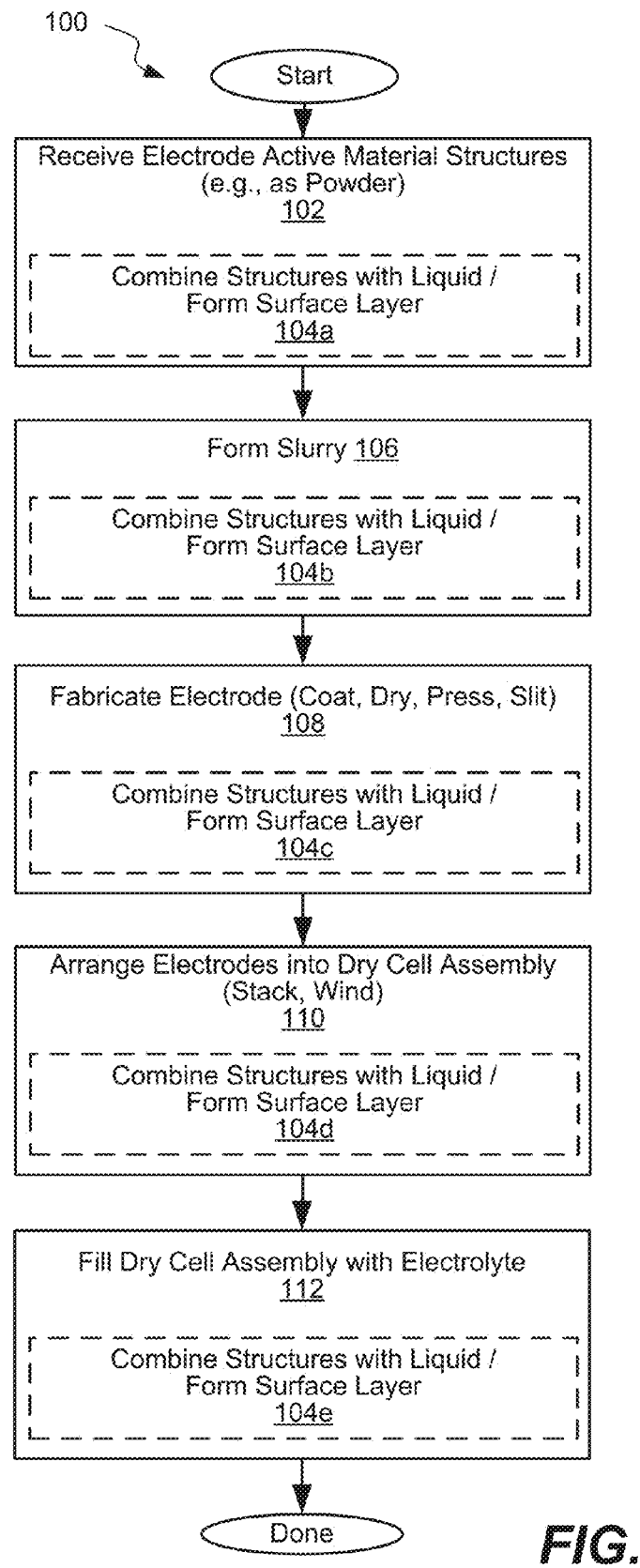
FIG. 1 is a process flowchart corresponding to a method of forming a surface layer on electrode active material structures, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

INTRODUCTION

Electrolyte decomposition in an electrochemical cell often occurs on a surface of electrode active material structures resulting in gas evolution and/or an increase in resistance of the cell. The gas evolution can cause swelling of the cell, rapturing of the case of the cell, and even fire and/or explosion of the cell if the gas evolution is not controlled or prevented. Furthermore, the increase in the resistance of the cell negatively impacts its rate capabilities and capacity.

The disclosed embodiments help to overcome these problems by forming a surface layer on electrochemical active material structures, thereby preventing or at least minimizing a direct contact between the active material surface and an electrolyte. The surface layer operates as a barrier between the active material and the electrolyte. As a result, a less reactive surface of the surface layer is exposed to the electrolyte instead of a more reactive surface of the active material.

A surface layer is formed when electrode active material structures are combined with a liquid to form a mixture. The surface layer is covalently bound to the structures. This feature helps to maintain the surface layer on the surface of the structures when, for example, the structures are subjected to further processing or undergo operation (e.g., lithiation and delithiation). The mixture may include one or more surface reagents. The surface reagents may be a part of the liquid that is combined with the structures or added into the mixture after the structures are combined with the liquid. The electrode active material structures may be provided as a powder, as a part of a standalone electrode (e.g., a partially assembled electrode), or as a part of an electrode arranged into a stack or a jelly roll. For example, electrode active material structures may be provided as a powder and treated in a mixture to form a surface layer. The structures with the surface layer may be then extracted from the mixture and formed into a powder for future uses. Alternatively, electrode active material structures may be provided as a powder and mixed into a slurry used for electrode fabrication. A surface reagent may be added into the slurry (e.g., prior to coating the slurry onto a current collecting substrate). A surface layer is formed on the electrode active material structures that are part of the slurry and then part of the electrode. In this example, the structures with the surface layer are not returned back into a powder form. Alternatively, the liquid combined with electrode active material structures may be an electrolyte introduced into a dry cell assembly. The mixture of the structures and the liquid is formed when an electrode containing the structures is soaked in the electrolyte, thereby allowing the structures to come in contact with the surface reagent. The electrolyte may include other components, such as lithium containing salts, solvents, and the like.

Surface layers are configured to be less reactive with electrolyte components than is active material itself. In other words, a surface layer reduces the reactivity of electrode active material structures to which it is bound. To illustrate this difference in reactivity, reaction mechanisms will now be briefly described for typical active materials and electrolyte components. Without wishing to be bound by a particular theory, it is believed that metal oxides of nickel, cobalt, aluminum, titanium, and manganese can catalyze decomposition of electrolyte components and, in particular, electrolyte solvents. For example, carbonates, such as ethylene carbonate (EC), dimethyl carbonate (DMC), methyl ethyl carbonate (MEC), diethyl carbonate (DEC), and solvents that are commonly used for battery electrolytes, can oxidize on the surface of many metal oxides at high potentials (e.g., greater than 4.0V, 4.5V or 5.0V). Such potentials are common for many positive electrodes. Lithium titanium oxide, which is used for negative electrodes, includes oxide and hydroxide groups on its surface. The oxide groups are believed to be responsible for absorption of solvent molecules on the surface of lithium titanium oxide particles. The solvents may then decompose and release hydrogen and other gaseous products, thereby converting the oxide groups into hydroxide groups. At the same time, hydroxide groups of lithium titanium oxide may undergo a reduction and release of hydrogen, which goes into the gas phase. Other electrode active materials are often imparted by surface species that introduce undesirable effects in the functioning or fabrication of the batteries.

In addition, the performance of the material or battery may be impaired by traces of moisture. Reducing or fully eliminating this moisture can be beneficial. For example, a surface layer formed on electrode active material structures may reduce hydrophobicity of the structures. As a result, the structures may adsorb less moisture from the environment when stored as a powder (raw materials), as parts of an electrode, and/or as a part of dry cell assembly.

In some embodiments, oxide groups and/or hydroxide groups, which otherwise are present on the surface of untreated electrode active material structures, are converted into blocking functional groups of a surface layer. For example, a surface reagent may include a blocking functional group, which may be attached to a supporting group. For purposes of this document, the blocking functional group may be also referred to as a remaining group as it remains a part of the surface layer. The supporting group may be referred to as a leaving group as it does not remain a part of the surface layer. In some embodiments, the leaving group may be removed from the mixture by, e.g., drying or vacuuming. Alternatively, the leaving group may remain in an electrode or other type of assembly without being covalently bound to electrode active material structures. Returning to the above example, the blocking functional group may replace the hydrogen of the hydroxide groups on the surface of the active materials. As such, the blocking functional group may be attached to oxygen, which in turn is attached to the surface of the active material.

The blocking functional group may be selected to be less reactive than hydrogen with respect to electrolyte components. The reduction in reactivity may be attributed, for example, to larger sizes of the blocking functional groups. In some embodiments, blocking functional groups include silane groups, aluminum isopropoxide, titanium isopropoxide, or combinations thereof. These and other examples are further described below.

Without being restricted to any particular theory, removal or blocking of hydroxide groups on the surface of electrode active material structures with a less reactive surface layer is believed to be one mechanism for reducing decomposition and/or oxidation of electrolyte. Another mechanism is deactivating the lithium metal oxide surface reactivity. Electrochemical cells assembled with treated electrode active material structures demonstrate improved performance in comparison to cells assembled with untreated electrode active material structures as described in the experimental result section below. Specifically, the cells assembled with the treated electrode active material structures demonstrated superior high temperature stability, surface stability, rate capability, stability towards electrolytes at higher voltages, compatibility with particular solvents (such as propylene carbonate or other carbonate, ester or ionic liquid based solvent), and increased functionality in solutions containing electrolyte salts (such as lithium imides, $LiPF_6$, $LiBF_4$, LiBOB) in comparison with cells assembled with the same but untreated structures.

Furthermore, forming a surface layer on electrode active material structures may also decrease metal dissolution of the active material and reduce catalytic activity towards electrolyte, thereby achieving a corresponding reduction in parasitic reactions and self-discharge. A stable interface between the electrode active material structures and electrolyte may also result in improved durability in terms of crystal structure breakdown. If a surface of untreated electrode active material structures is exposed to electrolyte, the metal from the metal oxide may dissolve/leach out. This, in turn, can affect the crystal structure of the active material on the surface. However, treated electrode active material structures tend to be more stable.

Some active materials, particularly certain positive materials, undergo significant morphological rearrangements at certain stages of the charge-discharge cycle. For example, the crystallographic lattice structure may fundamentally transform from one state of charge to another as the electrode goes to a deep discharge. Sometimes, the electrode active material structures may mechanically crack under the stress created by changes in the crystal structure. This cracking may be prevented by modifying the structure or morphology of the particle surfaces while preserving the native structure in the core. As an example, particles having a principal dimension of about 30-40 nm are modified to a depth of about 1-5 nm at their surfaces. Treated electrode active material structures are believed to either not exhibit or exhibit substantially less of the characteristic crystallographic reorientations during cycling.

Processing Examples

Forming surface layers on electrode active material structures may be performed at different stages of fabricating electrode active materials or using electrode active materials for fabricating electrodes and cells as described below with reference to FIG. 1. The stage at which the surface layers are formed may be selected based on the type of the electrode active material (e.g., its composition, morphology, shape of structures, size of structures), processing conditions, and other factors. It has been found that using the same surface reagent at different stages produces different kinds of surface layers, which was evident from the different performances of assembled cells as further described below in the experimental results section. For purposes of this document, forming surface layers on electrode active material structures may be also referred to as surface treatment of these electrode active material structures. These specific surface layers are covalently bound to their electrode active material structures. As such, the type of surface treatments described herein should be distinguished from other surface treatments when, for example, surface layers are not formed or newly formed surface layers are not covalently bound to their structures.

FIG. 1 is a process flowchart corresponding to method 100 of a surface treatment of electrode active material structures or, more specifically, forming a surface layer on these electrode active material structures, in accordance with some embodiments. The surface layer is formed or at least starts forming when the structures are combined with a liquid to form a mixture that contains a surface reagent as shown by operations 104a, 104b, 104c, 104d, and 104e. A surface layer may be formed at any one of these operations. Of course, different liquids are used and different mixtures are formed depending on which operation is used for forming a surface layer.

In some embodiments, only one of these operations 104a, 104b, 104c, 104d, and 104e is performed to form a surface layer on electrode active material structures. Alternatively, two or more of operations 104a, 104b, 104c, 104d, and 104e may be performed. When multiple operations are used for forming a surface layer, the initial operation may form a partial surface layer that is later modified or added to in one or more subsequent operations to form a final surface layer. For example, a partial surface layer may be formed during operation 104a and later modified during operation 104b.

Some of operations 104a, 104b, 104c, 104d, and 104e may be parts of other operations used to fabricate electrodes and/or cell assemblies. Alternatively, some of these operations may be standalone operations. For example, surface treatment during operation 104a may be performed on electrode active material structures received in a powder form (and before these structures are combined with a polymer binder to form slurry). A surface reagent may be a part of the liquid specially designed to treat the powder and, in some embodiments, to yield a powder after processing. In addition to the surface reagent, this liquid may include other components, such as one or more solvents and/or one or more catalysts. The mixture formed when the liquid is combined with the electrode active material structures is then processed to recover electrode active material structures with a formed surface layer.

As such, operation 104a may be a standalone operation and not integrated into another operations used to fabricate electrodes or cell assemblies. Alternatively, operation 104a may be implemented as a part of electrode active material structure fabrication (e.g., during final stages of processing).

Surface treatment during operation 104c may be performed on a partially assembled electrode (e.g., a coated current collector) or a fully assembled electrode (e.g., a pressed and slit electrode) before the electrode is arranged into a stack or a jelly roll with one or more other electrodes. Operation 104c may also be a standalone operation that is performed during or after electrode fabrication. A surface reagent may be a part of the liquid specially designed to treat electrodes.

Surface treatment during operation 104d may be performed on a stack or a jelly roll, which may be collectively referred to as a dry cell assembly, prior to introducing an electrolyte into this assembly. Again, operation 104d may be a standalone operation. A surface reagent may be a part of the liquid specially designed to treat dry cell assemblies. For example, the liquid may include one or more solvents that easily evaporate without a need for excessive temperatures, which are damaging to the separator of the dry cell assembly. The liquid may be removed from the dry cell assembly at the end of operation 104d.

On the other hand, operation 104b and/or operation 104e may be performed as a part of standard fabrication operations. Specifically, operation 104b may be a part of slurry mixing and electrode coating. During this operation, the electrode active material structures may be received as a part of a slurry that is later coated onto a current collecting substrate. A surface reagent may be added into the slurry after or before the electrode active material structures are added into the slurry. In some embodiments, a surface reagent may be a part of a component forming the slurry (e.g., pre-mixed with a solvent).

In another example presented by operation 104e, electrode active material structures are received as a part of a dry cell assembly or, more specifically, as one or more electrodes arranged with one or more other electrodes into the dry cell assembly. A surface reagent may be added as a part of an electrolyte solution (e.g., a liquid), which is used to fill the cell. As such, the electrode active material structures are combined with a liquid containing a surface reagent when the electrolyte has soaked the one or more electrodes containing the structures. For purposes of this document, the one or more electrodes containing the structures, soaked with the electrolyte containing the surface agent, are referred to as a mixture.

Overall, electrode active material structures may be provided as a powder during operations 102 and/or 106, as a part of an electrode (full or partially fabricated) during operation 108, and as a part of a dry cell assembly ready to be filled with an electrolyte during operations 110 and 112. In some embodiments, surface layers may be formed on electrode active material structures before these structures are combined with other electrode materials to form slurry or, more specifically, before these structures are combined with a polymer binder. This example is illustrated by a combination of operations 102 and 104a in FIG. 1. At this stage of the processing, electrode active material structures received during operation 102 may be referred to as a raw material. In some embodiments, the received structures may be pre-mixed with one or more conductive additives, such as graphite, acetylene black, carbon nanotubes, ceramics, other electrode active materials, and the like, prior to surface treatment. Pre-mixing may be used, for example, for coating of active material structures with carbon additives.

During operation 104a, the electrode active material structures provided during operation 102 are combined with a liquid to form a mixture. In some embodiments, the liquid already includes a surface reagent prior to forming the mixture. Alternatively, the surface agent may be added into the mixture after the liquid is combined with the electrode active material structures. The amount of the surface reagent may depend on the size and shape of electrode active material structures or, more specifically, on the surface area of these structures that needs to be covered with a surface layer. For example, smaller particles may require more surface reagent, while larger particles may need less. The ranges provided herein are generally applicable for electrode active material structures having an average size of between about 1 micron and about 50 microns. These particles can be macrostructures made of smaller particles, sometimes called crystallines, of 0.04 micron to 0.4 micron. In some embodiments, the amount of surface reagent in the mixture is between about 0.1% by weight and about 10% by weight relative to the weight of the electrode active material structures or, more specifically, between about 0.25% by weight and about 5% by weight or even between about 0.5% by weight and about 2% by weight. These amounts are believed to create a conformal monolayer on the surface of the structures and to avoid excess surface reagent in the mixture that has not reacted or otherwise attached to the surface of the structures. Various examples of surface reagents are presented below. The ranges of the surface reagent described above are also applicable to surface reagents used in operations 104b, 104c, 104d, and 104e as further described below.

In addition to a surface reagent, the liquid used in operation 104a may include a solvent and, in some embodiments, a catalyst. Some examples of solvents may include polar protic solvents and aprotic solvents, such as ethanol, N-methylpyrrolidone (NMP), acetonitrile, acetone, isopropanol, dimethyl formamide, dimethyl sulfoxide, ethyl acetate, methanol, and other like solvents. Without being restricted to any particular theory, it is believed that such solvents improve the reaction yield (i.e., of a chemical reaction during which the surface reagent forms the surface layer), while aprotic hydrophobic solvents (polar or non-polar) may reduce the yield, for example, when oxy-silanes are used as surface reagents. In some embodiments, the amount of solvent in the liquid used to treat electrode active material structures during operation 104a is between about 100% by weight and about 600% by weight relative to the weight of the structures or, more specifically, between about 200% by weight and about 400% by weight, such as about 300%. While more solvent is generally desirable for thorough wetting of electrode active material structures, the excessive solvent may be difficult to separate from the structures, and it may cause low concentrations of the surface reagent in the mixture.

In some embodiments, water may be used as a catalyst during operation 104a and/or possible other surface treatment operations. Adding a small amount of water to a mixture containing, for example, an oxy-silane is believed to hydrolyze the silane group and facilitate the reaction of the active material surface groups with the hydrolyzed silane. In some embodiments, the amount of water in the mixture is between about 0.1% by weight and about 10% by weight relative to the weight of the electrode active material structures or, more specifically, between about 0.25% by weight and about 5% by weight or even between about 0.5% by weight and about 2% by weight. Excessive amounts of water may unfavorably shift the reaction equilibrium and may not yield a desirable surface layer.

The electrode active material structures may be combined with the liquid by mixing these two components and forming a mixture or, more specifically, a suspension during operation 104a. This mixture should be distinguished from a slurry that may be provided, for example, during operation 106. This mixture includes a surface reagent, which may be provided as a part of the liquid or added into the mixture after the electrode active material structures are combined with the liquid. The electrode active material structures may be actively suspended in the liquid by continuous mixing, thereby ensuring adequate contact between the structures and the surface reagent. The mixing may continue for between about 10-60 minutes. In some embodiments, the mixture can be heated to improve reaction kinetics but without shifting the thermodynamic reaction equilibrium. The electrode active material structures may then be filtered and washed one or more times (e.g., twice) with a solvent used in the liquid (e.g., ethanol). The filtered structures may then be dried to remove remaining components of the liquid. For example, the electrode active material structures may be dried at a temperature of between about 80° C. and about 140° C. for between about 4 hours and 24 hours or, more specifically, at a temperature of about 120° C. for about 16 hours. Overall, when surface layers are formed on electrode active material structures at this stage, the structures may be separated from the liquid and formed into, for example, a powder before using these structures for electrode fabrication. The dried electrode active material structures may be ready for use in later operations, such as operation 106. Operation 104a may be performed by a raw material supplier, by an electrode manufacturer, or by a battery manufacturer.

In some embodiments, operation 104a is not performed and method 100 proceeds from operation 102 directly to operation 106. On the other hand, if operation 104a is performed, it may be the only surface treatment operation in the entire method 100 or combined with one or more other surface treatment operations 104b, 104c, 104d, and 104e.

Method 100 may then proceed with operation 106, during which electrode active material structures are combined with other electrode materials to form slurry. During this operation, the structures are at least combined with at least a polymer binder. However, other materials, such as conductive additives and/or solvents, may be added to the mixture to form the slurry. Slurry formulation depends on desired performance characteristics of the battery (e.g., rate capability, capacity), electrode active material (e.g., composition, size of structures), and other factors. Slurry formulation would be understood by one having ordinary skills in the art. The surface reagent may be added into the fully formulated slurry (i.e., all other components of the slurry present) or partially formulated slurry (e.g., some components other than active materials structures are missing). For example, in the latter case, the remaining solvent and/or binder may be added after adding the surface reagent. In the partially formulated slurry, the same amount of the surface reagent will have a high concentration than in the fully formulated slurry. The high concentration may be desirable from the kinetics and/or thermodynamics perspective. In the latter case, most of the surface layer may be formed before adding the remaining components into the slurry.

Operation 104b may be a part of operation 106. In this example, the mixture that contains a surface reagent is the slurry. It should be noted that the surface reagent may be added (e.g., into the liquid or another component) prior to forming the slurry or after the slurry is formed. In either case, the surface reagent eventually comes in contact with the structures and forms the surface layer covalently bound to these structures. In some embodiments, the surface layer may start forming when the slurry is formed (e.g., components of the slurry are mixed together). In some embodiments, the slurry is mixed for between about 10 minutes and 60 minutes while the electrode active material structures and the surface reagent are both present in the slurry. The slurry may be outgassed to remove reaction products (e.g., gases generated during formation of the surface layer). Furthermore, the slurry may be heated for a period of time (prior to coating the slurry on a current collecting substrate) to speed up the formation of the surface layer. In some embodiments, formation of the surface layer continues even after the slurry is coated on the current collecting substrate. Coating provides additional mixing of the slurry, while drying of the coating heats up the slurry and may speed up formation of the surface layer.

In some embodiments, operation 104b is not performed. On the other hand, if operation 104b is performed, it may be the only surface treatment operation in the entire method 100 or combined with one or more other surface treatment operations 104a, 104c, 104d, and 104e.

Method 100 may then proceed with fabricating an electrode during operation 108. This operation involves a series of steps, such as coating slurry onto a current collecting substrate, drying the slurry to form an initial active material layer, compressing the layer to achieve a desirable density, slitting the electrode to its final width and length. The current collecting substrate may receive one or two electrode active material layers during operation. These layers are initially formed when the current collecting substrate is coated with the slurry and dried. The layers may be then pressed to the right density. In some embodiments, electrode active material structures are treated to form a surface layer while they are part of an electrode active material layer.

For purposes of this document, an electrode assembly is referred to as a structure at any stage of operation 108. As such, the electrode assembly covers both fully fabricated electrodes and partially fabricated electrodes. For example, operation 104c may be performed on the electrode assembly prior to its compressing, after compressing but prior to slitting, or after slitting. A liquid containing the surface reagent may be dispensed over each active material layer of the electrode assembly. In some embodiments, the electrode assembly is dipped (partially or completely) into the liquid. The liquid is allowed to soak into active material layers to ensure contact between the surface reagent and the electrode active material structures. The liquid may be heated to between about 50° C. and 100° C. Overall, a presence of polymer binders, such as polyvinylidene fluoride, carboxymethyl cellulose (or a salt of carboxymethyl cellulose), and styrene butadiene rubber, may limit the processing temperature to less than 200° C., or sometimes less than 170° C. and even less than 130° C. because higher temperatures may melt or degrade the binder material.

Furthermore, a temporary electrochemical cell may be formed during operation 104c to conduct the surface treatment of an electrode assembly. The electrode assembly may be submerged into a liquid that contains charge carrying ions. In some embodiments, charge carrying ions may be formed by a surface reagent. A voltage may be applied to the current collecting substrate of the electrode assembly to ensure the flow of the ions in the temporary cell.

In some embodiments, operation 104c is not performed. On the other hand, if operation 104c is performed, it may be the only surface treatment operation in the entire method 100 or combined with one or more other surface treatment operations 104a, 104b, 104d, and 104e.

Method 100 may then proceed with arranging electrodes into a dry cell assembly, such as a stack or a jellyroll, during operation 110. This operation may involve winding two electrodes together with separator sheets or stacking electrodes with separator sheets. Operation 110 will be understood by one having ordinary skills in the art.

At least one of these arranged electrodes includes electrode active material structures. Surface layers may be already formed on these electrode active material structures during, for example, one or more of operations 104a, 104b, and 104c. Alternatively, the electrode active material structures may not yet have electrode active material structures. In some embodiments, surface layers may be formed on electrode active material structures after two or more electrodes are arranged into the dry cell assembly, for example, in operation 104d (i.e., prior to introducing an electrolyte into the dry cell assembly). During operation 104d, a liquid containing a surface reagent may be introduced in a way similar to filling an electrolyte. However, the liquid may be at least partially removed. In some embodiments, after the surface layer is formed, most of the liquid is removed from the dry cell assembly. For example, a surface reagent may be dissolved in a solvent that is later evaporated leaving the surface reagent on the surface of the cell components. In some embodiments, any unreacted surface reagent may be also removed from the dry cell assembly by, for example, evaporation or subsequent washing of the assembly with a solvent and drying the assembly. Similar to the electrode treatment, treatment of the arranged electrodes may involve electrochemical reactions. The treatment temperature during operation 104d is limited by the separator and/or other temperature sensitive components that may be presented in the assembly. In some embodiments, the temperature used in operation 104d is between about 30° C. and about 100° C. or, more specifically, between about 40° C. and about 80° C. Higher temperatures may cause separator degradation. In some embodiments, temperatures as high as 120° C. and even as high as 180° C. and even 200° C. may be used with some separator materials. For example, high temperature separators including cellulose, polyethylene terephthalate, or aramid may be used, thereby allowing higher temperatures. The same temperature considerations are applicable to operation 104e further described below.

In some embodiments, operation 104d is not performed. On the other hand, if operation 104d is performed, it may be the only surface treatment operation in the entire method 100 or combined with one or more other surface treatment operations 104a, 104b, 104c, and 104e.

Method 100 may then proceed with filling the dry cell assembly with electrolyte during operation 112. The dry cell assembly may include a pouch or a case for containing the electrolyte. In some embodiments, operation 112 may include outgassing. Operation 112 may include operation 104e, such that the surface layers are formed on the electrode active material structures when one or more electrodes containing these structures and arranged into the dry cell assembly come in contact with the electrolyte. A surface reagent may be a part of the electrolyte. In other words, surface treatment is carried out when the cell is filled with the electrolyte containing the surface reagent. Formation of the surface layer may continue during initial formation cycling and even during later operational cycling.

In some embodiments, operation 104e is not performed and surface layers are formed on electrode active material structures during one or more of operations 104a, 104b, 104c, and 104d. On the other hand, if operation 104e is performed, it may be the only surface treatment operation in the entire method 100 or combined with one or more other surface treatment operations 104a, 104b, 104c, and 104d.

The duration of the treatment depends on the reactivity of the material surface towards the surface reagent. In some embodiments, the contact time between the electrode active material structures and the surface reagent is no longer than about 72 hours or, more specifically, no longer than about 24 hrs, no longer than 2 hours, or even no longer than about 30 minutes.

Regardless of the stage of the surface treatment, combining the electrode active material structures with a liquid may be performed within a short duration after drying the structures, e.g., exposing the structures to above 100° C. under a vacuum to reduce absorbed moisture. In some embodiments, that duration (i.e., between drying and surface treating) may be less than about 24 hours, less than about 4 hours, or even less than about 1 hour to prevent post-drying adsorption of moisture and, in some embodiments, formation of lithium carbonates on the surface of the electrode active material structures. In addition or instead of this limited duration, contact with air or, more specifically, with moisture in the air may be prevented by using dry gases, moisture barrier packaging, and other such techniques.

Additionally, other types of processing may be used in conjunction with combining the electrode active material structures with the liquid in order to facilitate the reaction or provide an additional reaction/transformation. Such processing may be conducted either at the same time as, prior to, or after the reaction of the reactive solution to the active material suspension. Example of such other processing may include high-temperature treatments, irradiation with x-rays or other forms of electromagnetic radiation, ultrasonic agitation, other forms of mechanical stimulation, and so forth. For example, when electrode active material structures are treated as a powder, the structures may undergo mechanical disruption to enhance the surface treatment and/or achieve more thorough treatment. As specific examples, the structures may be stirred, shaken, ball-milled, blown or otherwise dispersed. Other treatment methods may include X-ray radiation or ultraviolet (UV) radiation, e.g., to cross-link polymer coating disposed on surfaces of active material structures.

Optionally, the liquid/solid phase reaction may be performed with one or more accompanying procedures that do not directly facilitate chemical transformation of the active material surface. Such additional procedures may be performed immediately prior to or immediately after the surface modification reaction. As used herein, immediately prior to or immediately after means that the two procedures occur without an additional procedure in between. In certain implementations, however, there may be a waiting time between the two procedures. It may be necessary, for example, to remove by-products produced by the surface modification reaction. Other requirements may include drying the active material, physically or chemically activating the material, and so forth.

Pre-reaction processing can include, but is not limited to, drying by heating or calcination, exposure to a vacuum, or both. Additionally, the material may be pre-processed by ball-milling, sintering or other mechanical treatments.

Post-reaction treatment can include, but is not limited to, removing the products of the reactions by heating, exposure to a vacuum, flushing with inert gas, or repetitive vacuum-air flush steps. Alternatively, the treated materials or materials incorporated into the electrodes can be washed in one or more aqueous or organic solvents.

Various surface conditions of electrode active material structures can be treated in accordance with the methods described above. Among these conditions are excess moisture, the presence of reactive hydroxide groups, the presence of potentially soluble metal ions (e.g., $Mn^{2+}$, $Mn^{3+}$, $Co^{2+}$, and $Ni^{2+}$) in the form of oxides or salts, the presence of carbonate, and the presence of potentially reactive oxides (e.g., titanate). For example, some positive active material oxides such as lithium manganese oxide, lithium nickel oxide, lithium nickel manganese cobalt oxide, and lithium nickel cobalt aluminum oxide, are believed to lose soluble metal ions (e.g., $Mn^{2+}$, $Mn^{3+}$, $Co^{2+}$, or $Ni^{2+}$) to the electrolyte during normal cell operation. Surface layers formed when electrode active material structures are treated in accordance with the methods described above may trap the metal compounds in or on the electrode, thereby preventing dissolution or leeching of the compound into the electrolyte during battery operation. The trapping may be accomplished by, for example, reacting metal hydroxides on the surface with a compound that than reacts with another like compound to form a cross-linked, conformal network. Thus, in some embodiments, the surface treatment includes exposure of the active material to a compound that can react with the active material surface and then crosslink with itself. In some embodiments, surface hydroxyls and oxides on the surface of particles of the negative electrode material are reacted with a hydrolyzed silane that contains additional hydroxyl groups that can react with other silane groups through a hydrolysis reaction.

Figure 3A:
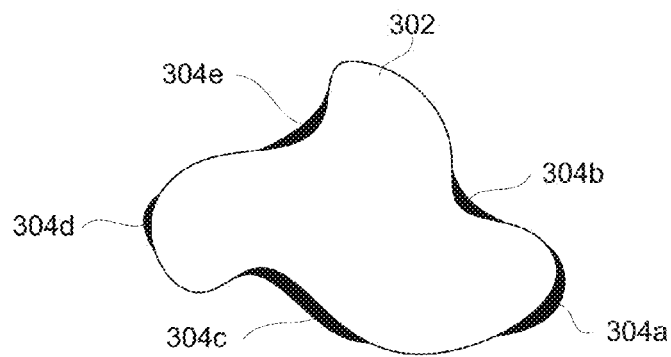
FIGS. 3A-3C are schematic representations of electrode active material structures having surface layers, in accordance with some embodiments.
Figure 3B:
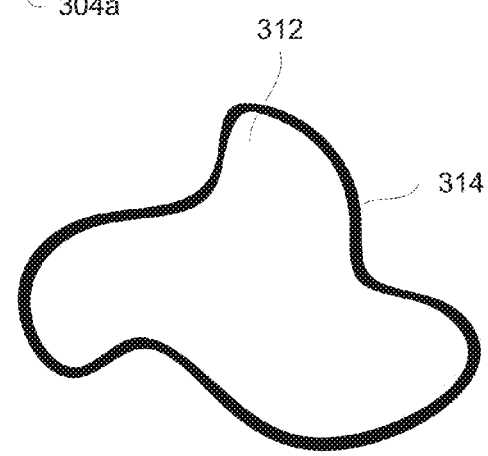
Figure 3C:
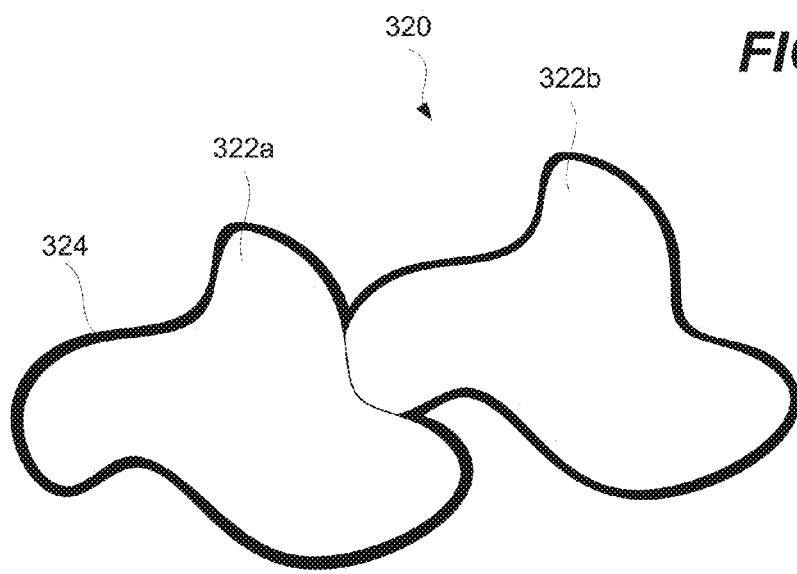

FIGS. 3A-3C are schematic representations of electrode active material structures having surface layers, in accordance with some embodiments. Specifically, FIG. 3A illustrates an electrode active material structure 302 having a surface layer formed by patches 304a-304e. It should be noted that the surface layer does not need to be a continuous structure fully encapsulating structure 302. The surface reactivity may be significantly reduced even though only a portion of the surface of structure 302 is covered with the surface layer. The uncoated portions may provide some electrolyte access to structure. FIG. 3B illustrates an electrode active material structure 312 having a continuous surface layer 314 fully encapsulating structure 312. Finally, FIG. 3C illustrates an aggregate 320 of two electrode active material structures 322a and 322b having a continuous surface layer 324 fully encapsulating aggregate 320 but not each structure individually.

Electrochemical Active Material Examples

Various methods described herein can be used to modify the surface of the negative active material structures and positive active material structures, which are collectively referred herein as electrode active material structures. Typically, though not necessarily, the electrode active material structures are configured for fabrication into a lithium ion battery or components thereof (e.g., electrodes). Any of the electrode active material structures may be treated in their lithiated or delithiated state. In some embodiments, e.g., when a surface reagent is a part of the electrolyte, the structures may form a surface layer as they undergo lithiation and/or delithiation. Further, when treated, these structures may have a morphology, shape, and size appropriate for battery applications, whether fully fabricated (e.g., completed cells) or partially fabricated (e.g., electrodes during fabrication).

Illustrative shapes of these electrode active material structures include round particles, squared particles, needles, plates, sheets, fibers, hollow tubes, porous particles, dense particles, flakes, spheres, and combinations of any of these. Illustrative average particle sizes are about 10 nanometers to about 50 micrometers, or about 1 micrometer to about 10 micrometers. Lithium titanate electrode material particles tend to have relatively small average dimensions, e.g., about 10 nanometers to about 400 nanometers, and they may sometimes have agglomerates of about 1 micrometer to about 10 micrometers. The average values presented here represent the average largest/principal dimension of the particles. Some types of particles are not substantially spherical (e.g., they are shaped as flakes, rods, ovals, pillows, etc.) and therefore have two or more dimensions. It should also be noted that some materials have a large variance in particle size, with some particles being substantially larger or smaller than the endpoints of the average ranges set forth above.

The negative electrode active materials include materials capable of intercalating or inserting an alkali metal ion such as lithium or sodium ions. Some of these materials are deployed in commercial lithium ion batteries, while others are under investigation for lithium ion batteries. Examples of negative active materials that can be surface modified in accordance with the methods disclosed herein include carbons (e.g., graphite, fullerenes, and graphene), silicon, tin, titanium, germanium, the oxides of any of these, the alloys of any of these, and the like.

The method can also be applied to modify the surface of various types of positive active materials. Classes of positive electrode materials include $LiMO_2$, $LiMPO_4$, $LiM_2O_4$, a lithium metal silicide, $MS_x$ (metal sulfide), $M_xO_y$ (metal oxide) where M is a metal such as V, Mn, Fe, Co, Ni, Al, Si, or a combination thereof. Examples of lithium metal oxides include $LiCoO_2$, $LiMnO_2$, lithium nickel oxides such as $LiNiO_2$, $LiNi_xCo_{1-x}O_2$, $LiNi_xCo_yMn_{(1-x-y)}O_2$, $LiNi_xCo_yAl_{(1-x-y)}O_2$ whereas $0<x<1$, $0<y<1$, lithium metal phosphates, and lithium mixed metal phosphates such as $LiFePO_4$, $LiMnPO_4$, $LiCoPO_4$, $LiFe_xMn_{1-x}PO_4$, $LiNi_xMn_{1-x}O_4$. The method can also be applied to decrease the amount of remaining moisture in materials, electrodes or cells before filling them with electrolyte.

Specific groups of electrode active materials include a group of titanium containing materials and a group of nickel containing materials. Both groups of these materials are believed to be responsible for significant gas evolution if these materials are not treated in accordance with techniques described above. Specific examples of the titanium containing materials include LTO and variations thereof. Specific examples of the nickel containing materials include lithium nickel oxides such as $LiNiO_2$, $LiNi_xCo_{1-x}O_2$, $LiNi_xCo_yMn_{(1-x-y)}O_2$, $LiNi_xCo_yAl_{(1-x-y)}O_2$ whereas $0<x<1$, $0<y<1$.

Examples of Liquids and Surface Reagents

As noted above, electrode active material structures are combined with a liquid to form a mixture. The mixture includes a surface reagent that forms a surface layer covalently bound to the electrode active material structures. The surface reagent may be added as a part of the liquid before the liquid is combined with the structure. Alternatively, the surface reagent may be added into the mixture (i.e., after the electrode active material structures are combined with the liquid).

Liquid phases in comparison to gas phases allow using a new range of surface reagents and form new types of surface layers. For example, some chemical reactions need liquid solvents in order to proceed because, for example, the solvent may lower activation energies of these surface layer forming reactions. Furthermore, liquid phases tend to be easier to handle and often safer to process than, for example, various gas phase reactions.

The liquid may include one or more solvents or other materials that provide a liquid phase. The surface reagent may be dissolved in the liquid, may form a suspension (e.g., in which the surface reagent remains in the solid phase), or may form a mixture of two liquids (e.g., in which the surface is immiscible in the solvent). As examples, the solvent soluble surface reagents may include compounds containing carbon, oxygen, fluorine, sulfur, nitrogen, and phosphorous. Compounds containing chlorine or some other halogens can be used as well. However, sometimes halogens should be avoided in certain battery systems as they may result in poisoning of the electrode materials. Halogen containing compounds can form acids such as HF, HCl, or HBr that may attack current collecting substrates of positive and negative electrodes, the metal can, and other active materials in a cell. For certain materials, metal containing compounds such as titanium isopropoxide and aluminum isopropoxide can be used.

The weight ratio of the surface reagent to the liquid may depend on reactivity of the surface reagent, desirable weight ratio of the surface reagent to the electrode active material structures, processing stage (powder, slurry, electrode, electrolyte), and other factors. In some embodiments, a surface reagent may be diluted with a liquid to control its reactivity. For example, the weight ration of MTMS in a liquid may be between about 1:200 to 1:1. In this example, the liquid may be ethanol if the electrode active material structures are treated as a powder or NMP if the structures are treated in slurry.

Additionally, solvent choice may affect reaction kinetics depending on the type of reaction being used for the active material surface modification. For example, nucleophilic substitutions with small negatively charged nucleophiles are much more rapid in aprotic polar solvents than in protic solvents. In some embodiments, the reactive compounds may be applied to the active material without solvent.

Surface reagents include compounds that are capable of reacting with the surface of the electrode active material or reacting at the surface, e.g., when the surface is operable as a catalyst and not as one of the reagents. Some examples of surface reagents include acyl halides, aldehydes, alkyl halides, amides, anhydrides, aryl halides, carboxylic acids, diazo compounds, enol esters, enol ethers, esters, ethers, isocyanates, isothiocyanates, lactones, Michael acceptors, nitriles, phosphorous halides, silanes, sulfonamides, sulfonyl chlorides, sulfur trioxides, thionyl halides, and functionalized versions thereof. Many other inorganic compounds based on phosphorus, sulfur and boron can be utilized, as well. In some embodiments, the surface reagent may be or may include an oxy-silane. More specifically, the surface reagent may be a trioxy-silane represented by the following general formula of R—Si(OR')$_3$, where R is one of H, $(CH_2)_X CH_3$, $CH=CH_2$, $(CH_2)_X(CF_2)_Y CF_3$, $(CH_2)_X Si(OCH_3)_3$, $(CH_2)_X(N_2C_3H_5)$, and $(CH_2)_X PO_3$ with X ranging from 0 to 15 and Y ranging from 0 to 5. R may be referred to as a remaining group since it becomes a part of a surface layer. R' may be referred to as a leaving group and may bind with hydrogen of a hydroxyl group of electrode active material structures and be removed from the cell. Usually, R' is one of H or a small alkyl group (e.g., $(CH_2)_X CH_3$ with X ranging from 0 to 5).

In some embodiments, R is H or $CH_3$. These small size groups are more reactive with the surface groups (e.g., hydroxyl groups) of electrode active material structures due to their higher surface reaction probability in comparison, for example, to larger groups. Furthermore, these small groups provide good surface coverage and form surface layers having a lower resistance than, for example, surface layers formed from larger groups. However, surface layers formed from these small groups may be also more permeable to electrolyte materials (e.g., carbonates) than, for example, surface layers formed from larger molecules.

In some embodiments, R is $(CH_2)_X CH_3$ with X ranging from 5 to 15. Surface layers formed from these larger groups are less permeable to electrolyte materials (e.g., carbonates) than, for example, surface layers formed from smaller molecules as described above. However, surface layers formed from these larger groups tend to have high electrical resistance and provide less coverage.

In some embodiments, R is $CH=CH_2$. Without being restricted to any particular theory, it is believed that the vinyl group and a small size may provide more conformal coverage of the resulting surface layer in comparison to other groups described above. Furthermore, the double bond may help to establish additional crosslinking in the surface layer. However, the vinyl group may be too reactive for some treatment options, and remaining double bonds may be react with the electrolyte in an undesirable way.

In some embodiments, R is $(CH_2)_X(CF_2)_Y CF_3$ with X ranging from 0 to 15 and Y ranging from 0 to 5. Without being restricted to any particular theory, it is believed that fluorinated surface layers have excellent stability on a surface of many negative electrode active materials used in lithium ion batteries. For example, fluorine containing surface reagents may be used on lithium titanate and its derivatives. However, if alkyl or fluoro-alkyl chains are too long, the resulting surface layer may be not sufficiently conformal and/or electrically conductive.

In some embodiments, R is $(CH_2)_X Si(OCH_3)_3$, with X ranging from 0 to 15. Use of this remaining group will yield di-silane surface layers, which are believed to provide good surface coverage and inhibit electrolyte component access to electrode active material structures. However, one of the silane groups may not react as intended. The reaction of the second oxy-silane on the reagent will be dependent on access available to the surface of the same particle or another particle. Steric and proximity effects may play a role in the second group not reacting.

In some embodiments, R is $(CH_2)_X(N_2C_3H_5)$, with X ranging from 0 to 15. In this example, $(N_2C_3H_5)$ is an imidazole ion having a cyclic group formed by two carbon atoms and three nitrogen atoms with one double bond between one of the carbon atoms and one of the nitrogen atoms. In addition to the silane reaction with, for example, hydroxyl groups on the surface of electrode active material structures, the basic amine sites are believed to decrease gassing in some of the electrode active materials, such as LTO.

In some embodiments, R is $(CH_2)_X PO_3$ with X ranging from 0 to 15. Phosphorous groups are believed to aid in forming low impedance surface films. However, the coverage may not be as good as with some other groups described above.

Figure 2A:
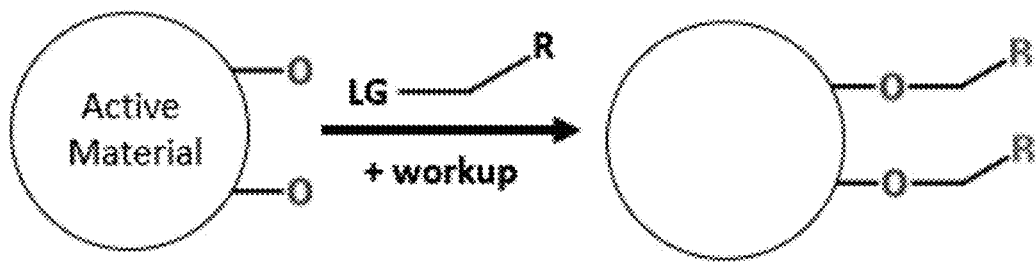
FIGS. 2A-2C are proposed mechanisms of forming surface layers on electrode active material structures, in accordance with some embodiments.

Mechanisms of forming surface layers using some of these surface reagents will now be described with reference to FIGS. 2A-2C. Specifically, FIG. 2A illustrates an electrode active material particle having oxide groups interacting with surface reagents having both leaving groups and remaining groups. The remaining groups bind to oxygen atoms, thereby blocking these oxygen atoms and preventing them from reacting with electrolyte components. The leaving group may be removed from the processing environment or may remain as a part of a batter component. In the latter case, the leaving group may form a sufficiently inert material.

Figure 2B:
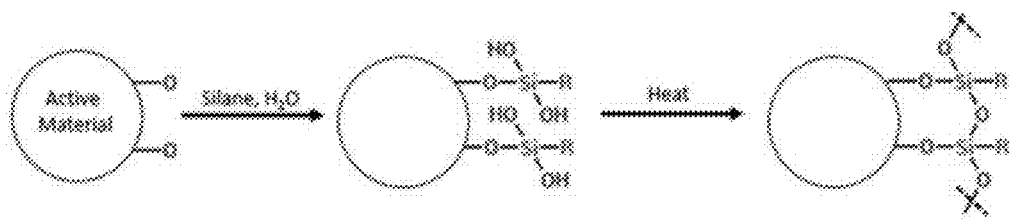
Figure 2C:
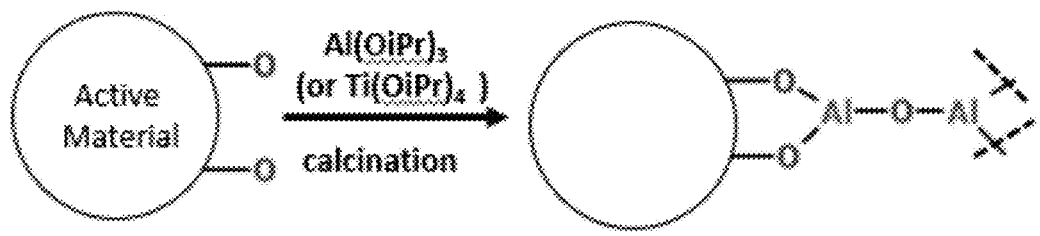

In the mechanism presented in FIG. 2B, a trioxy-silane is formed when a remaining group binds to the oxygen atoms present on the surface of the electrode active materials particles. The oxide or hydroxyl group will act to hydrolyze (displacement reaction) the previously hydrolyzed silane to form a covalent bond. In FIG. 2C, parts of aluminum isopropoxide or titanium isopropoxide bind to the oxygen atoms present on the surface of the electrode active materials particles after calcination forming aluminum oxide or titanium oxide complexes.

Addition of a third component may also promote the desired reaction sequence. For instance, adding a small amounts of water to a solution of MTMS in ethanol will hydrolyze the silane group and facility reaction of the active material surface groups with the hydrolyzed silane.

Examples of Electrochemical Cells

Figure 4:
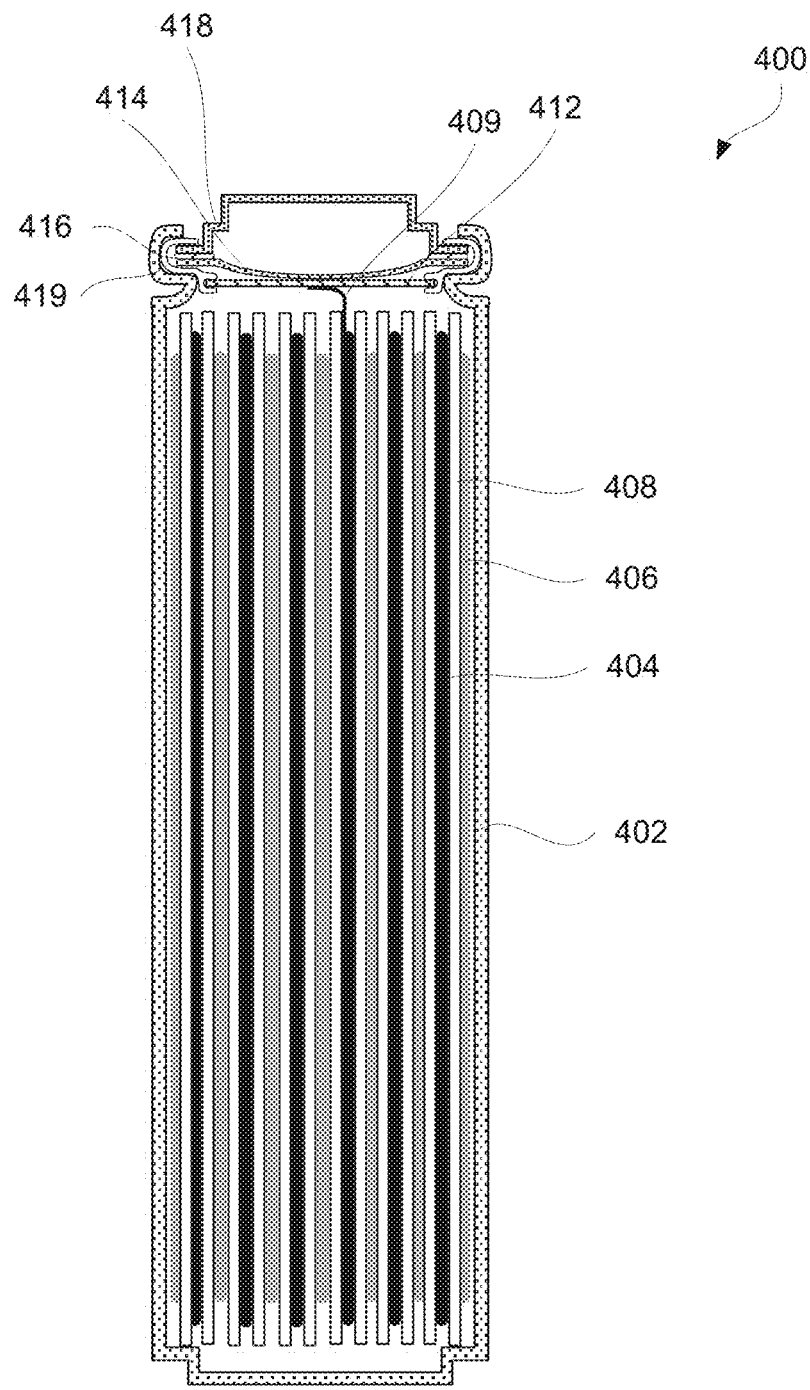
FIG. 4 is a schematic representation of an electrochemical cell, in accordance with certain embodiments.

A brief description of a cell is provided for better understanding of some electrolyte features as well as components that come in contact with electrolyte and expose electrolyte to certain potentials. FIG. 4 illustrates a schematic cross-sectional view of a cylindrical wound cell 400, in accordance with some embodiments. Positive electrode 406, negative electrode 404, and separator strips 408 may be wound into a jelly roll, which is inserted into a cylindrical case 402. The jelly roll is a spirally wound assembly of positive electrode 406, negative electrode 404, and two separator strips 408. The jelly roll is formed into a shape of case 402 and may be cylindrical for cylindrical cells and a flattened oval for prismatic cells. Other types of electrode arrangements include stacked electrodes that may be inserted into a hard case or a flexible case.

The electrolyte (not shown) is supplied into case 402 prior to sealing cell 400. The electrolyte soaks into positive electrode 406, negative electrode 404, and separator strip 408, all of which are porous components. The electrolyte provides ionic conductivity between positive electrode 406 and negative electrode 404. As such, the electrolyte is exposed to the operating potentials of both electrodes and comes in contact with essentially all internal components of cell 400. The electrolyte should be stable at these operating potentials and should not damage the internal components.

Case 402 may be rigid (in particular for lithium ion cells). Other types of cells may be packed into a flexible, foil-type (polymer laminate) case. For example, pouch cells are typically packed into a flexible case. A variety of materials can be chosen for case 402. Selection of these materials depends in part on an electrochemical potential to which case 402 is exposed to. More specifically, the selection depends on which electrode, if any, case 402 is connected to and what the operating potentials are of this electrode.

If case 402 is connected to positive electrode 406 of a lithium ion battery, then case 402 may be formed from titanium 6-4, other titanium alloys, aluminum, aluminum alloys, and 300-series stainless steel. On the other hand, if case 402 is connected to negative electrode 404 of the lithium ion battery, then case 402 may be made from titanium, titanium alloys, copper, nickel, lead, and stainless steels. In some embodiments, case 402 is neutral and may be connected to an auxiliary electrode made, for example, from metallic lithium. An electrical connection between case 402 and an electrode may be established by a direct contact between case 402 and this electrode (e.g., an outer wind of the jelly roll), by a tab connected to the electrode and case 402, and other techniques. Case 402 may have an integrated bottom as shown in FIG. 4. Alternatively, a bottom may be attached to the case by welding, soldering, crimping, and other techniques. The bottom and the case may have the same or different polarities (e.g., when the case is neutral).

The top of case 402, which is used for insertion of the jelly roll, may be capped with a header assembly that includes a weld plate 412, a rupture membrane 414, a washer 416, header cup 418, and insulating gasket 419. Weld plate 412, rupture membrane 414, PCT washer 416, and header cup 418 are all made from conductive material and are used for conducting electricity between an electrode (negative electrode 404 in FIG. 4) and a cell connector. Insulating gasket 419 is used to support the conductive components of the header and insulate these components from case 402. Weld plate 412 may be connected to the electrode by tab 409. One end of tab 409 may be welded to the electrode (e.g., ultrasonic or resistance welded), while the other end of tab may be welded to weld plate 412. Centers of weld plate 412 and rupture membrane 414 are connected due to the convex shape of rupture membrane 414. If the internal pressure of cell 400 increases (e.g., due to electrolyte decomposition and other outgassing processes), rupture membrane 414 may change its shape and disconnect from weld plate 412, thereby breaking the electrical connection between the electrode and the cell connector.

PCT washer 416 is disposed between edges of rupture membrane 414 and edges of header cup 418 effectively interconnecting these two components. At normal operating temperatures, the resistance of PCT washer 416 is low. However, its resistance increases substantially when PCT washer 416 is heated up due to, e.g., heat released within cell 400. PCT washer 416 is effectively a thermal circuit breaker that can electrically disconnect rupture membrane 414 from header cup 418 and, as a result, disconnect the electrode from the cell connector when the temperature of PCT washer 416 exceeds a certain threshold temperature. In some embodiments, a cell or a battery pack may use a negative thermal coefficient (NTC) safety device in addition to or instead of a PCT device.

Also provided herein are battery packs, each containing one or more electrochemical cells built with processed active materials. When a battery pack includes multiple cells, these cells may be configured in series, in parallel, or in various combinations of these two connection schemes. In addition to cells and interconnects (electrical leads), battery packs may include charge/discharge control systems, temperature sensors, current balancing systems, and other like components. For example, battery regulators may be used to keep the peak voltage of each individual cell below its maximum value so as to allow weaker batteries to be fully charged, thereby bringing the whole pack back into balance. Active balancing can also be performed by battery balancer devices that can shuttle energy from stronger batteries to weaker ones in real time for improved balance.

Electrode Active Materials and Electrolytes

In certain embodiments, a positive electrode includes one or more active materials and a current collecting substrate. The positive electrode may have an upper charging voltage of about 3.5-4.5 volts versus a $Li/Li^+$ reference electrode. The upper charging voltage is the maximum voltage to which the positive electrode may be charged at a low rate of charge and with significant reversible storage capacity. In some embodiments, cells utilizing a positive electrode with upper charging voltages from about 3-5.8 volts versus a $Li/Li^+$ reference electrode are also suitable. In certain instances, the upper charging voltages are from about 3-4.2 volts, about 4.0-5.8 volts, or about 4.5-5.8 volts. In certain instances, the positive electrode has an upper charging voltage of about 5 volts. For example, the cell can have an upper charging voltage of about 4.9, 5.0, 5.1, 5.2, 5.3, 5.4, 5.5, 5.6, 5.7 or 5.8 volts. A variety of positive electrode active materials can be used. Non-limiting illustrative electrode active materials include transition metal oxides, phosphates and sulfates, and lithiated transition metal oxides, phosphates and sulfates.

In some embodiments, the electrode active materials are oxides with empirical formula $Li_xMO_2$, where M is a transition metal selected from Mn, Fe, Co, Ni, Al, Mg, Ti, V, Si of a combination thereof, with a layered crystal structure. The value x may be between about 0.01 and about 1, between about 0.5 and about 1, or between about 0.9 and about 1.

In other embodiments, the electrode active materials are oxides with the formula $Li_xM1_aM2_bM3_cO_2$, where M1, M2, and M3 are each independently a transition metal selected from the group Mn, Fe, Co, Ni, Al, Mg, Ti, V or Si. The subscripts a, b and c are each independently a real number between about 0 and 1 ($0 \leq a \leq 1$; $0 \leq b \leq 1$; $0 \leq c \leq 1$; $0.01 \leq x \leq 1$), with the proviso that a+b+c is about 1.

In certain instances, the electrode active materials are oxides with the empirical formula $Li_xNi_aCo_bMn_cO_2$, wherein the subscript x is between about 0.01 and 1 (e.g., x is 1); the subscripts a, b and c are each independently 0, 0.1, 0.2, 0.3, 0.4, 0.5, 0.6, 0.7, 0.9 or 1, with the proviso that a+b+c is 1. In other instances, the subscripts a, b and c are each independently between about 0-0.5, between about 0.1-0.6, between about 0.4-0.7, between about 0.5-0.8, between about 0.5-1 or between about 0.7-1 with the proviso that a+b+c is about 1.

In yet other embodiments, the active materials are oxides with the empirical formula $Li_{1+x}A_yM_{2-y}O_4$, where A and M are each independent transition metal selected from Fe, Mn, Co, Ni, Al, Mg, Ti, V, Si, and a combination thereof, with a spinel crystal structure. The value x may be between about −0.11 and 0.33, or between about 0 and about 0.1. The value of y may be between about 0 and 0.33, or between 0 and about 0.1. In one embodiment, A is Ni, x is 0 and y is 0.5 (i.e., the active material is $LiA_{0.5}M_{1.5}O_4$).

In yet some other embodiments the active materials are vanadium oxides such as $LiV_2O_5$, $LiV_6O_{13}$, or the foregoing compounds modified in that the compositions thereof are nonstoichiometric, disordered, amorphous, overlithiated or underlithiated.

The suitable positive electrode-active compounds may be further modified by doping with about 5% or less of divalent or trivalent metallic cations such as $Fe^{2+}$, $Ti^{2+}$, $Zn^{2+}$, $Ni^{2+}$, $Co^{2+}$, $Cu^{2+}$, $Mg^{2+}$, $Cr^{3+}$, $Fe^{3+}$, $Al^{3+}$, $Ni^{3+}$, $Co^{3+}$, or $Mn^{3+}$, and the like. In other embodiments, positive electrode active materials suitable for the positive electrode composition include lithium insertion compounds with olivine structure such as $Li_xMXO_4$, where M is a transition metal selected from Fe, Mn, Co, Ni, and a combination thereof, X is a selected from P, V, S, Si and combinations thereof, and the value of the value x is between about 0 and 2. In certain instances, the compound is $LiMXO_4$. In some embodiments, the lithium insertion compounds include $LiMnPO_4$, $LiVPO_4$, $LiCoPO_4$ and the like. In other embodiments, the active materials have NASICON structures such as $Y_xM_2(XO_4)_3$, where Y is Li or Na, or a combination thereof, M is a transition metal ion selected from Fe, V, Nb, Ti, Co, Ni, Al, or the combinations thereof, X is selected from P, S, Si, and combinations thereof, and the value of x is between 0 and 3. Examples of these materials are disclosed by J. B. Goodenough in "Lithium Ion Batteries" (Wiley-VCH press, Edited by M. Wasihara and O. Yamamoto). Particle size of the electrode materials may be between about 1 nm and about 100 μm, or between about 10 nm and about 100 μm, or between about 1 μm and 100 μm.

In other embodiments, the electrode active materials are oxides such as $LiCoO_2$, spinel $LiMn_2O_4$, chromium-doped spinel lithium manganese oxides $Li_xCr_yMn_2O_4$, layered $LiMnO_2$, $LiNiO_2$, or $LiNi_xCo_{1-x}O_2$, where x is between about 0 and 1, or between about 0.5 and about 0.95. The electrode active materials may also be vanadium oxides such as $LiV_2O_5$, $LiV_6O_{13}$, or the foregoing compounds modified in that the compositions thereof are nonstoichiometric, disordered, amorphous, overlithiated or underlithiated.

The suitable positive electrode-active compounds may be further modified by doping with about 5% or less of divalent or trivalent metallic cations such as $Fe^{2+}$, $Ti^{2+}$, $Zn^{2+}$, $Ni^{2+}$, $Co^{2+}$, $Cu^{2+}$, $Mg^{2+}$, $Cr^{3+}$, $Fe^{3+}$, $Al^{3+}$, $Ni^{3+}$ $Co^{3+}$, or $Mn^{3+}$, and the like. In yet other embodiments, positive electrode active materials suitable for the positive electrode composition include lithium insertion compounds with olivine structure such as $LiFePO_4$ and with NASICON structures such as $LiFeTi(SO_4)_3$. In still other embodiments, electrode active materials include $LiFePO_4$, $LiMnPO_4$, $LiVPO_4$, $LiFeTi(SO_4)_3$, $LiNi_xMn_{1-x}O_2$, $LiNi_xCo_yMn_{1-x-y}O_2$ and derivatives thereof, wherein x and y are each between about 0 and 1. In certain instances, x is between about 0.25 and 0.9. In one instance, x is ⅓ and y is ⅓. Particle size of the positive electrode active material should range from about 1 to 100 microns.

In some embodiments, the electrode-active material includes transition metal oxides such as $LiCoO_2$, $LiMn_2O_4$, $LiNiO_2$, $LiNi_xMn_{1-x}O_2$, $LiNi_xCo_yMn_{1-x-y}O_2$ and their derivatives, where x and y are each between about 0 and 1. $LiNi_xMn_{1-x}O_2$ can be prepared by heating a stoichiometric mixture of electrolytic $MnO_2$, LiOH and nickel oxide to between about 300 and 400° C. In certain embodiments, the electrode active materials are $xLi_2MnO_3(1-x)LiMO_2$ or $LiM'PO_4$, where M is selected Ni, Co, Mn, $LiNiO_2$ or $LiNi_xCo_{1-x}O_2$; M' is selected from Fe, Ni, Mn and V; and x and y are each independently a real number between about 0 and 1. $LiNi_xCo_yMn_{1-x-y}O_2$ can be prepared by heating a stoichiometric mixture of electrolytic $MnO_2$, LiOH, nickel oxide and cobalt oxide to between about 300 and 500° C. The positive electrode may contain conductive additives from 0% to about 90%. In one embodiment, the subscripts x and y are each independently selected from 0.1, 0.15, 0.2, 0.25, 0.3, 0.35, 0.4, 0.45, 0.5, 0.55, 0.6, 0.65, 0.7, 0.75, 0.8, 0.85, 0.9 or 0.95, and x and y can be any numbers between 0 and 1 to satisfy the charge balance of the compounds $LiNi_xMn_{1-x}O_2$ and $LiNi_xCo_yMn_{1-x-y}O_2$.

Representative positive electrodes and their approximate recharged potentials include $FeS_2$ (3.0 V vs. $Li/Li^+$), $LiCoPO_4$ (4.8 V vs. $Li/Li^+$), $LiFePO_4$ (3.45 V vs. $Li/Li^+$), $Li_2FeS_2$ (3.0 V vs. $Li/Li^+$), $Li_2FeSiO_4$ (2.9 V vs. $Li/Li^+$), $LiMn_2O_4$ (4.1 V vs. $Li/Li^+$), $LiMnPO_4$ (4.1 V vs. $Li/Li^+$), $LiNiPO_4$ (5.1 V vs. $Li/Li^+$), $LiV_3O_8$ (3.7 V vs. $Li/Li^+$), $LiV_6O_{13}$ (3.0 V vs. $Li/Li^+$), $LiVOPO_4$ (4.15 V vs. $Li/Li^+$), $LiVOPO_4F$ (4.3 V vs. $Li/Li^+$), $Li_3V_2(PO_4)_3$ (4.1 V (2 Li) or 4.6 V (3 Li) vs. $Li/Li^+$), $MnO_2$ (3.4 V vs. $Li/Li^+$), $MoS_3$ (2.5 V vs. $Li/Li^+$), sulfur (2.4 V vs. $Li/Li^+$), $TiS_2$ (2.5 V vs. $Li/Li^+$), $TiS_3$ (2.5 V vs. $Li/Li^+$), $V_2O_5$ (3.6 V vs. $Li/Li^+$), and $V_6O_{13}$ (3.0 V vs. $Li/Li^+$) and combinations thereof.

A positive electrode can be formed by mixing and forming a composition including, by weight, between about 0.01-15% (e.g., between about 4-8%) polymer binder, between about 10-50% (e.g., between about 15-25%) electrolyte solution as herein described, between about 40-85% (e.g., between about 65-75%) electrode-active material, and between about 1-12% (e.g., between about 4-8%) conductive additive. An inert filler may also be added up to about 12% by weight, though in certain cases no inert filler is used. Other additives may be included, as well.

A negative electrode may include active materials and a current collecting substrate. The negative electrode includes either a metal selected from Li, Si, Sn, Sb, Al and a combination thereof, or a mixture of one or more negative electrode active materials in particulate form, a binder (in certain cases a polymeric binder), optionally an electron conductive additive, and at least one organic carbonate. Examples of useful negative electrode active materials include, but are not limited to, lithium metal, carbon (graphites, coke-type, mesocarbons, polyacenes, carbon nanotubes, carbon fibers, and the like), and LTO. Negative electrode-active materials also include lithium-intercalated carbon, lithium metal nitrides such as $Li_{2.6}Co_{0.4}N$, metallic lithium alloys such as LiAl, $Li_4Sn$, or lithium-alloy-forming compounds of tin, silicon, antimony, or aluminum. Further included as negative electrode-active materials are metal oxides such as titanium oxides, iron oxides, or tin oxides.

When present in particulate form, the particle size of the negative electrode active material should range from about 0.01 to 100 microns (e.g., from about 1 to 100 microns). In some cases the negative electrode active materials include graphites such as carbon microbeads, natural graphites, carbon nanotubes, carbon fibers, or graphitic flake-type materials. Alternatively or in addition, the negative electrode active materials may be graphite microbeads and hard carbon, which are commercially available.

A negative electrode can be formed by mixing and forming a composition including, by weight, between about 2-20% (e.g., 3-10%) polymer binder, between about 10-50% (e.g., between about 14-28%) electrolyte solution as described herein, between about 40-80% (e.g., between about 60-70%) electrode-active material, and between about 0-5% (e.g., between about 1-4%) conductive additive. In certain cases an inert filler is added up to about 12% by weight, although no filler is used in other cases. Additional additives may also be present.

Suitable conductive additives for the positive electrode and negative electrode composition include carbons such as coke, carbon black, carbon nanotubes, carbon fibers, and natural graphite, metallic flake or particles of copper, stainless steel, nickel or other relatively inert metals; conductive metal oxides such as titanium oxides or ruthenium oxides; or electrically-conductive polymers such as polyacetylene, polyphenylene and polyphenylenevinylene, polyaniline or polypyrrole. Additives may include, but are not limited to, carbon fibers, carbon nanotubes, and carbon blacks with a surface area below about $100\,m^2/g$, such as Super P and Super S carbon blacks available from MMM Carbon in Belgium.

The current collecting substrate suitable for the positive and negative electrode includes a metal foil and a carbon sheet selected from a graphite sheet, carbon fiber sheet, carbon foam, and carbon nanotube sheet or film. High conductivity is generally achieved in pure graphite and pure carbon nanotube films. Therefore, the graphite and nanotube sheeting should contain as few binders, additives, and impurities as possible in order to realize the benefits of the present embodiments. Carbon nanotubes can be present from about 0.01% to about 99% by weight. The carbon fiber can be in the micron or submicron range. Carbon black or carbon nanotubes may be added to enhance the conductivities of certain carbon fibers. In one embodiment, the negative electrode current collecting substrate is a metal foil, such as copper foil. The metal foil can have a thickness between about 5 and about 300 micrometers.

The carbon sheet current collecting substrate may be in the form of a powder coating on a substrate such as a metal substrate, a free-standing sheet, or a laminate. In other words, the current collecting substrate may be a composite structure having other members such as metal foils, adhesive layers, and such other materials as may be considered desirable for a given application. However, in any event, according to the present embodiments, it is the carbon sheet layer, or carbon sheet layer in combination with an adhesion promoter, which directly interfaces with the electrolyte and is in electrically conductive contact with the electrode surface.

Suitable binders include, but are not limited to, polymeric binders, particularly gelled polymer electrolytes including polyacrylonitrile, poly(methylmethacrylate), poly(vinyl chloride), and polyvinylidene fluoride, carboxymethylcellulose, and copolymers thereof. Also included are solid polymer electrolytes such as polyether-salt based electrolytes including poly(ethylene oxide)(PEO) and its derivatives, polypropylene oxide) (PPO) and its derivatives, and poly (organophosphazenes) with ethyleneoxy or other side groups. Other suitable binders include fluorinated ionomers including partially or fully fluorinated polymer backbones, and having pendant groups including fluorinated sulfonate, imide, or methide lithium salts. Specific examples of binders include polyvinylidene fluoride and copolymers thereof with hexafluoropropylene, tetrafluoroethylene, fluorovinyl ethers, such as perfluoromethyl, perfluoroethyl, or perfluoropropyl vinyl ethers; and ionomers including monomer units of polyvinylidene fluoride and monomer units including pendant groups including fluorinated carboxylate, sulfonate, imide, or methide lithium salts.

The electrochemical cell optionally contains an ion conductive layer or a separator. The ion conductive layer suitable for the lithium or lithium-ion battery of the present embodiments is any ion-permeable layer, preferably in the form of a thin film, membrane or sheet. Such ion conductive layer may be an ion conductive membrane or a microporous film such as a microporous polypropylene, polyethylene, polytetrafluoroethylene and layered structures thereof. Suitable ion conductive layers also include swellable polymers such as polyvinylidene fluoride and copolymers thereof. Other suitable ion conductive layers include gelled polymer electrolytes such as poly(methyl methacrylate) and poly(vinyl chloride). Also suitable are polyethers such as poly(ethylene oxide) and polypropylene oxide). In some cases, preferable separators are microporous polyolefin separators or separators including copolymers of vinylidene fluoride with hexafluoropropylene, perfluoromethyl vinyl ether, perfluoroethyl vinyl ether, or perfluoropropyl vinyl ether, including combinations thereof, or fluorinated ionomers.

An electrolyte may include various carbonates, such as cyclic carbonates and linear carbonates. Some examples of cyclic carbonates include ethylene carbonate (EC), propylene carbonate (PC), butylene carbonate (BC), vinylene carbonate (VC), dimethylvinylene carbonate (DMVC), vinylethylene carbonate (VEC), and fluoroethylene carbonate (FEC). The cyclic carbonate compounds may include at least two compounds selected from ethylene carbonate, propylene carbonate, vinylene carbonate, vinylethylene carbonate, and fluoroethylene carbonate. Some examples of linear-carbonate compounds include linear carbonates having an alkyl group, such as dimethyl carbonate (DMC), methyl ethyl carbonate (MEC), diethyl carbonate (DEC), methyl propyl carbonate (MPC), dipropyl carbonate (DPC), methyl butyl carbonate (MBC) and dibutyl carbonate (DBC). The alkyl group can have a straight or branched chain structure.

Examples of other non-aqueous solvents include lactones such as gamma-butyrolactone (GBL), gamma-valerolactone, and alpha-angelica lactone; ethers such as tetrahydrofuran, 2-methyltetrahydrofuran, 1,4-dioxane, 1,2-dimethoxyethane, 1,2-diethoxyethane, and 1,2-dibutoxyethane; nitriles such as acetonitrile, and adiponitrile; linear esters such as methyl propionate, methyl pivalate, butyl pivalate, hexyl pivalate, octyl pivalate, dimethyl oxalate, ethyl methyl oxalate, and diethyl oxalate; amides such as dimethylformamide; and compounds having an S=O bonding such as glycol sulfite, propylene sulfite, glycol sulfate, propylene sulfate, divinyl sulfone, 1,3-propane sultone, 1,4-butane sultone, and 1,4-butanediol dimethane sulfonate.

Examples of combinations of the non-aqueous solvents include a combination of a cyclic carbonate and a linear carbonate; a combination of a cyclic carbonate and a lactone;

a combination of a cyclic carbonate, a lactone and a linear ester; a combination of a cyclic carbonate, a linear carbonate, and a lactone; a combination of a cyclic carbonate, a linear carbonate, and an ether; and a combination of a cyclic carbonate, a linear carbonate, and a linear ester. Preferred are the combination of a cyclic carbonate and a linear carbonate, and the combination of a cyclic carbonate, a linear carbonate, and a linear ester.

Examples of electrolyte salts used in non-aqueous electrolytic solutions include: $LiPF_6$, $LiBF_4$, $LiClO_4$; lithium salts including a chain alkyl group such as $LiN(SO_2CF_3)_2$, $LiN(SO_2C_2F_5)_2$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, and $LiPF_5(iso-C_3F_7)$; and lithium salts including a cyclic alkylene group such as $(CF_2)_2(SO_2)_2NLi$, and $(CF_2)_3(SO_2)_2NLi$. More preferred are $LiPF_6$, $LiBF_4$ and $LiN(SO_2CF_3)_2$, and most preferred is $LiPF_6$, though these preferential ingredients are in no way limiting.

The electrolyte salt can be used singly or in combination. Examples of the preferred combinations include a combination of $LiPF_6$ with $LiBF_4$, a combination of $LiPF_6$ with $LiN(SO_2CF_3)_2$, and a combination of $LiBF_4$ with $LiN(SO_2CF_3)_2$. Most preferred is the combination of $LiPF_6$ with $LiBF_4$, though again, these preferential combinations are in no way limiting. There is no specific limitation with respect to the mixing ratio of the two or more electrolyte salts. In the case that $LiPF_6$ is mixed with other electrolyte salts, the amount of the other electrolyte salts preferably is about 0.01 mole % or more, about 0.03 mole % or more, about 0.05 mole % or more based on the total amount of the electrolyte salts. The amount of the other electrolyte salts may be about 45 mole % or less based on the total amount of the electrolyte salts, about 20 mole % or less, about 10 mole % or less, or about 5 mole % or less. The concentration of the electrolyte salts in the non-aqueous solvent may be about 0.3 M or more, about 0.5 M or more, about 0.7 M or more, or about 0.8 M or more. Further, the electrolyte salt concentration preferably is about 2.5 M or less, about 2.0 M or less, about 1.6 M or less, or about 1.2 M or less.

Experimental Results

A series of experiments have been conducted to determine the effects of surface treatment or, more specifically, effects of forming surface layers covalently bound to electrode active material structures on a performance of electrochemical cells fabricated with these structures.

LTO was used as a negative active material in these experiments. LTO is believed to catalyze certain reactions that result in gas evolution and an increased resistance of electrochemical cells. Specifically, the presence of hydroxyl groups on the surface of LTO structures is believed to cause electrolyte decomposition and degassing. Elimination or blocking of these hydroxyl groups should help to reduce outgassing and improve other characteristics.

MTMS was used as a surface reagent to form surface layers on the LTO structures. Without being restricted to any particular theory, it is believed that the hydroxide groups on the LTO surface react with MTMS thereby forming a siloxane containing surface layer.

A typical positive electrode was prepared using lithium manganese oxide (LMO), Super P, KS6 graphite, and PVDF. A matching negative electrode was fabricated using a slurry formed from LTO powder (available from Hanwha in Seoul, South Korea), KS6 graphite, Super P, PVDF, and N-Methyl-2-pyrrolidone. Prior to introducing a surface reagent, the slurry had 45% solid content. After mixing and final degas of the slurry (i.e., at the state when slurry is typically ready for coating), MTMS (Dynasylan MTMS available from Evonik Industries in Essen, Germany) was added to the slurry in an amount equal to 1% by weight based on the weight of LTO. The slurry was stirred to dissolve the MTMS in the NMP. Thin film coatings were cast on both sides of 16 micrometer thick aluminum foil. Each side had a loading of 10 mg/cm². The coating film was then compressed to a density of 1.8 g/cm³. A control LTO negative electrode, which did not have any MTMS added, was also prepared in an otherwise similar manner. The same positive electrode was used for both experimental and control cells.

Electrodes having a size of about 50 mm by 80 mm were punched from the pressed coated sheets. An uncoated strip of foil extended along one side of the electrode and used to attach tabs. The electrodes were then dried for 16 hours under a vacuum at 125° C. The electrodes were then arranged into stacks with a 20 micrometer thick polyethylene separator (available from W-Scope in Chungcheong-Do, Korea) and sealed in a laminated aluminum foil pouch. Each stack was disposed in a separate rectangular pouch with one side open and dried under a vacuum at 60° C. for 48 hours. The cells were then filled with electrolyte having the following formulation: 1 M $LiPF_6$, PC:EMC at a ratio of 1:4. The cells went through C/10 charge/discharge formation cycling with 1.5V and 2.7 V used as cut-off voltages, and were then vacuumed and sealed. The average cell impedance for the control cells (fabricated with the untreated LTO) was 42 mOhm, while the average cell impedance for the experimental cells (with the silane treated LTO) was 43 mOhm.

Figure 5A:
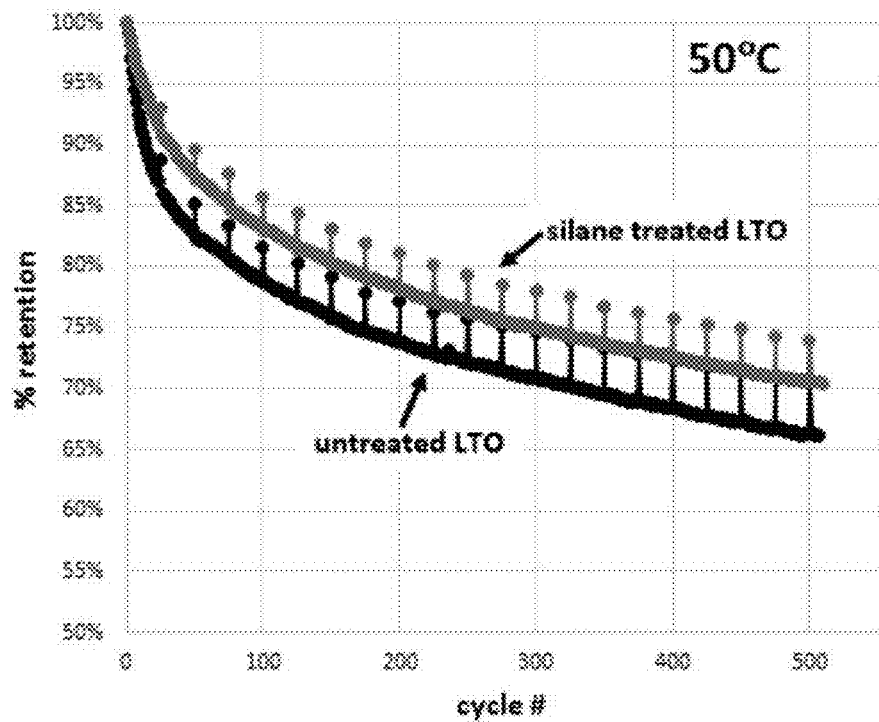
FIGS. 5A and 5B illustrate plots representing cycle life of electrochemical cells assembled using treated (in slurry) electrode active material structures and untreated electrode active material structures and cycled at 50° C. and 60° C.
Figure 5B:
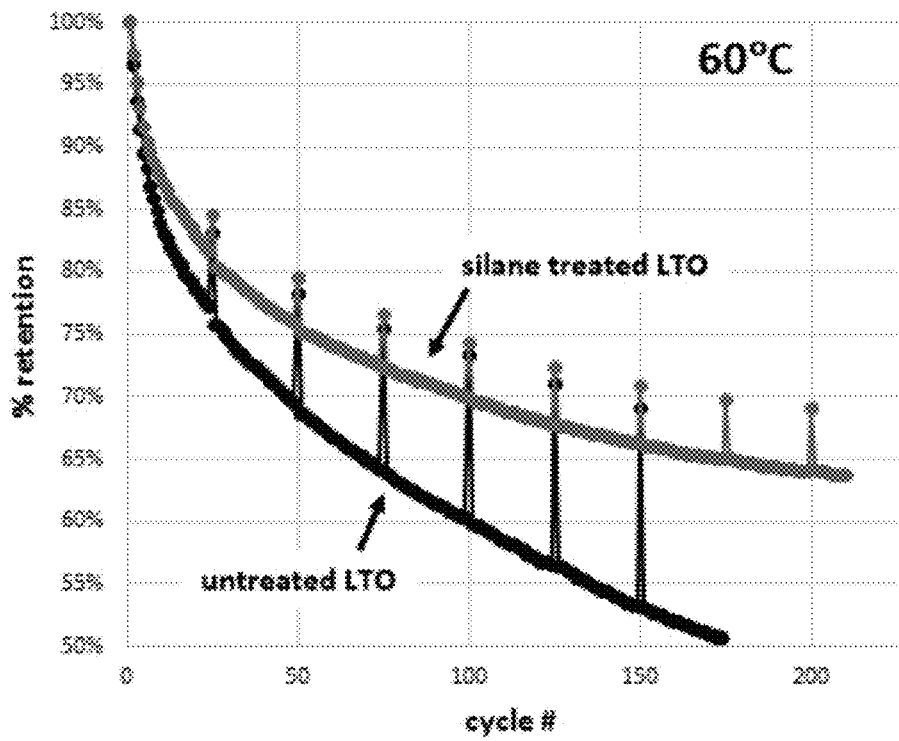

After these fabrication operations, the control cells and the experimental cells were subjected to cycle life testing at 50° C. and 60° C. to compare cycle life and stored at 60° C. and 100% state of charge (SOC) to compare swelling and impedance changes. FIG. 5A illustrates the cycle life data for the two types of cells cycled at 50° C. for about 500 cycles. Even after a few initial cycles, the experimental cells (with the silane treated LTO), which are represented by the top line, showed superior performance in comparison to the control cells (fabricated with the untreated LTO). The capacity retention was almost 5% greater for the experimental cells during most of the cycling test. The difference in performance was even more profound at higher temperatures. Specifically, FIG. 5B illustrates the cycle life data for the same two types of cells cycles at 60° C. At about 175 cycles, the capacity retention of the controlled cells fell below 50%, while the capacity retention of the experimental cells stayed at about 65%. Cycling was performed at a rate of 1 C charge with +2.7 V CVC with C/20 cutoff and a rate 1 C discharge with 15 min rests between charges and discharges.

Figure 6A:
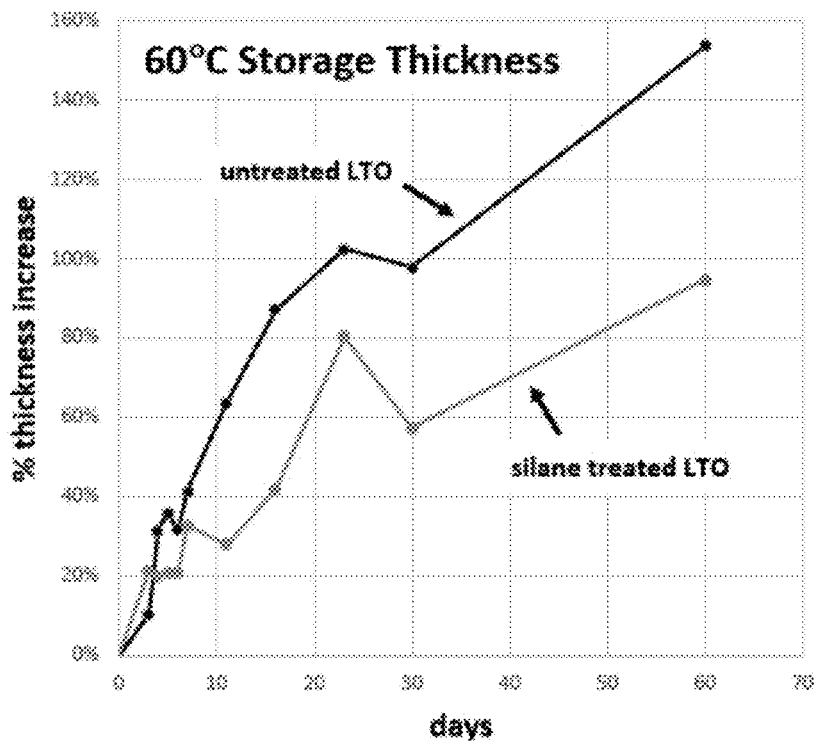
FIGS. 6A and 6B illustrate plots representing thickness change and capacity retention of electrochemical cells assembled using treated (in slurry) electrode active material structures and untreated electrode active material structures and stored at 60° C. and 100% state of charge.
Figure 6B:
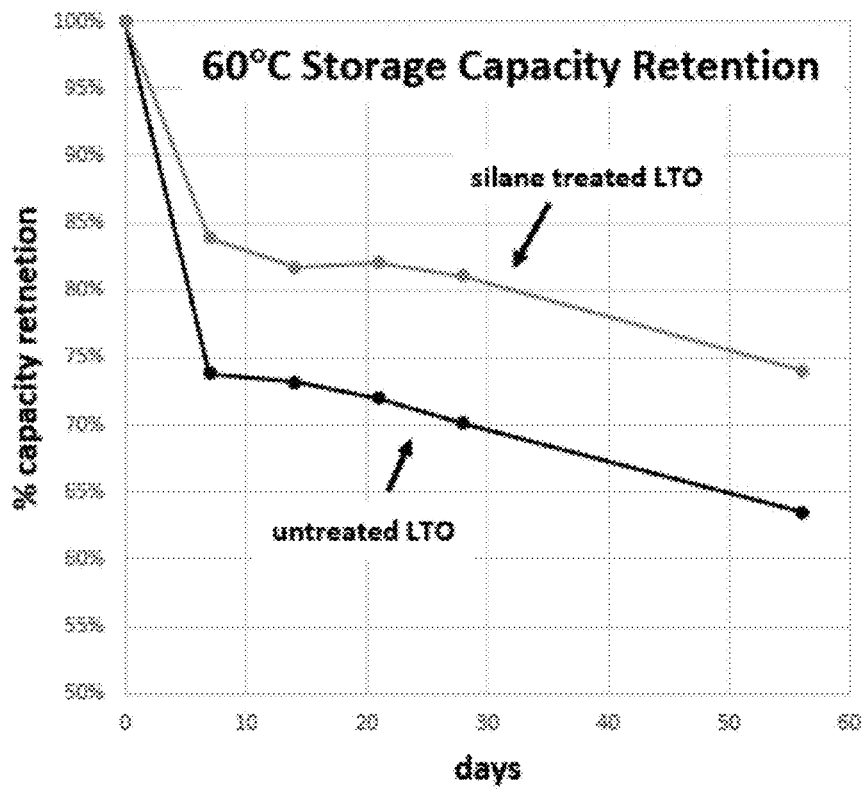

As noted above, in the storage test, after formation cycling, the experimental cells (with the silane treated LTO) and the control cells (fabricated with the untreated LTO) were charged to 100% SOC and stored at 60° C. for about 60 days. The thickness of the cells and capacity retention were monitored for these cells. The results are presented in FIGS. 6A and 6B. Specifically, FIG. 6A illustrates the thickness data. The control cells doubled their thicknesses (on average) after about 23 days of such storage, while the experimental cells have never reached this level of the thickness increase, even after 60 days of storage. FIG. 6B illustrates the capacity retention for the same two types of cells after different storage durations. The cells were discharged to 1.5 V from 100% SOC at the C/5 rate, and charged to 2.7 V at the C/5 rate followed by the discharge to 1.5 V at the C/5 rate. The last discharge capacity was used as a value in FIG. 6B. Subsequently, the cell was recharged to 2.7 V, 100% SOC for additional storage. The capacity retention was about 10% better for the experimental cells in comparison to the control cells. Overall, both swelling and capacity retention characteristics have improved with introduction of silane treatment of LTO.

In another experiment, MTMS was used to treat LTO while it was still in the powder form and prior to combining LTO structures with a polymer binder. This treatment is different from the one in the above described experiment, where MTMS was introduced into the slurry. The mechanism of forming a surface layer covalently bound to the LTO structures is believed to be the same.

Figure 7:
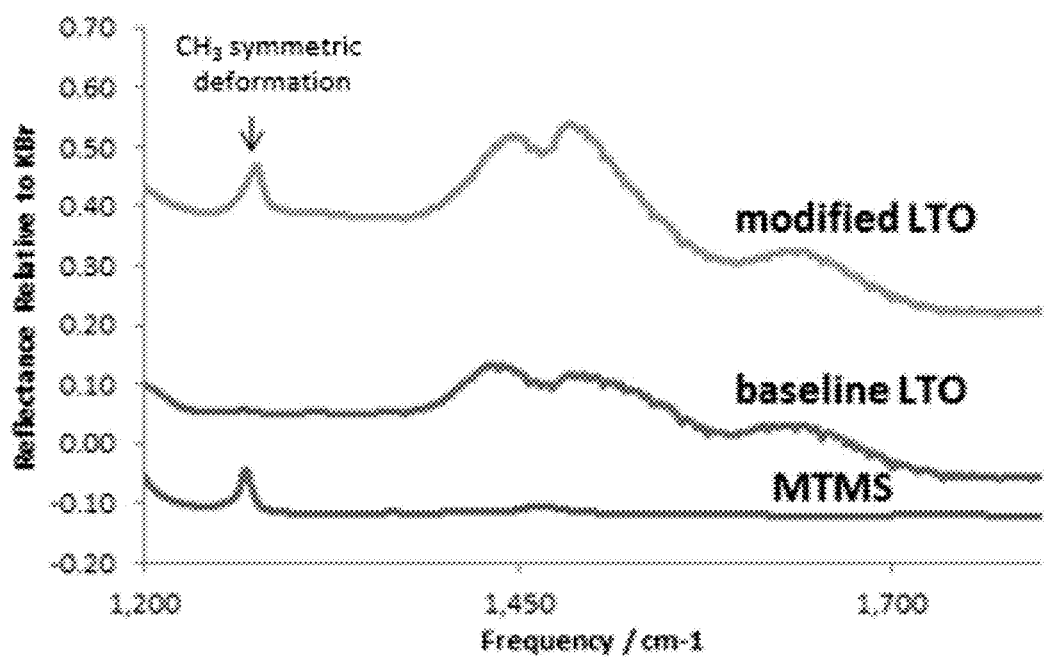
FIG. 7 illustrates infrared spectroscopy plots of trimethoxymethylsilane (MTMS), untreated LTO structures, and LTO structures treated (as a powder) with MTMS.

Before introducing the LTO into a slurry mix, the LTO powder was treated with MTMS. Specifically, the LTO powder, ethanol, and water were mixed together according to the following weight ratio of 1:3:0.01 for LTO:ethanol:water. Continuous mixing was used to keep the LTO particles constantly suspended. MTMS was added drop-wise so that a weight ratio of LTO:silane was 100:1. This mixture was stirred for 30 minutes. The powder was then filtered and washed twice with ethanol and finally dried for 16 hours at 120° C. under vacuum. FIG. 7 illustrates results of infrared spectroscopy for this silane modified LTO powder as well as for an untreated/baseline LTO powder, and separate results for MTMS. The results for the silane modified LTO illustrate a peak corresponding to the C—H bond typically found in methyl groups. The same peak was found for the MTMS sample, but not for the untreated/baseline LTO.

Figure 8:
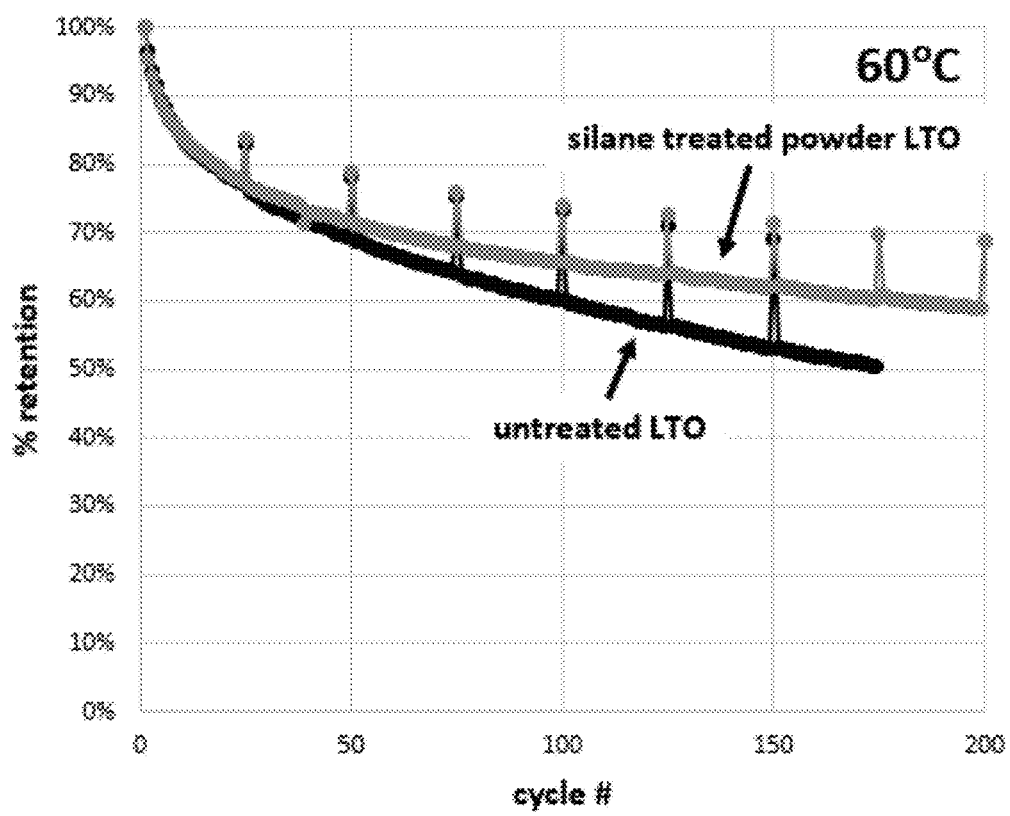
FIG. 8 illustrates plots representing cycle life of electrochemical cells assembled using treated (as a powder) electrode active material structures and untreated electrode active material structures cycled at 60° C.

In this second experiment, fabrication of positive and negative electrodes was similar to the test cells used in the first experiment. The only difference was that no MTMS was added to the negative slurry. After formation cycling, the control cells (without any LTO silane treatment) and the experimental cells (with the LTO silane treatment of the powder) were subjected to cycle life testing at 60° C. to compare cycles. The results are presented in FIG. 8. Similar to the results illustrated in FIG. 5B and described above, the capacity retention of the controlled cells fell below 50% after about 175 cycles. However, the capacity retention of the experimental cells stayed at about 60%. It should be noted that when silane treatment was performed by adding MTMS into slurry, the results were slightly better. As illustrated in FIG. 5B and described above, the capacity retention of the experimental cells fell with LTO structures treated at the slurry stage was about 65% after about 175 cycles.

In another experiment, a high molecular weight silane (Evonik 9116 available from Evonik Industries in Essen, Germany, molecular weight 346.62 g/mol) was added to the LTO powder in attempt to form a surface layer similar to the one formed with MTMS. For reference, the molecular weight of MTMS in the previous experiment was 136.22 g/mol. The treatment of the LTO powder was performed in a manner similar to MTMS treatment of the LTO powder described above. However, the silane 9116 treatment did not show any improvement in cycle life or swelling in comparison to the controlled cells. Without being restricted to any particular theory, it is believed that dry blending of treated powders causes mechanical scarping of surface layers previously formed on the electrode active material structures when these structures hit each other.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A method of forming a surface layer on negative electrode active material structures for a lithium ion battery, the method comprising:
   receiving the negative electrode active material structures, wherein the negative electrode active material structures are lithium titanium oxide; and
   combining the negative electrode active material structures with a liquid to form a mixture,
   adding a surface reagent into the mixture, wherein the surface reagent is an oxy-silane,
   the oxy-silane forming the surface layer covalently bound to the negative electrode active material structures, wherein the oxy-silane covalently bonds with titanium oxides of the lithium titanium oxide,
   the surface layer reducing reactivity of the negative electrode active material structures with respect to electrolyte components, and
   wherein the mixture comprising the oxy-silane is a slurry, the oxy-silane bonding with the lithium titanium oxide in the slurry to form the surface layer, the surface layer comprising siloxane.

2. The method of claim 1, wherein the negative electrode active material structures chemically react with the surface reagent, thereby forming the surface layer covalently bound to the negative electrode active material structures,
   or the negative electrode active material structures catalyze a chemical reaction involving the surface reagent such that the chemical reaction forms the surface layer covalently bound to the negative electrode active material structures.

3. The method of claim 1, wherein the slurry is configured for coating onto a current collecting substrate, and wherein the mixture further comprises a polymer binder selected from the group consisting of polyacrylonitrile, poly(methylmethacrylate), poly(vinyl chloride), polyvinylidene fluoride, poly(vinylidene fluoride-co-hexafluoropropene, polyacrylic acid, styrene butadiene rubber, carboxymethylcellulose and copolymers thereof.

4. The method of claim 3, further comprising coating the slurry onto the current collecting substrate and drying the slurry, thereby forming an electrode active material layer on the current collecting substrate.

5. The method of claim 1, wherein the surface reagent comprises a trioxy-silane having a general formula of R—Si(OR')$_3$, wherein R is selected from the group consisting of $(CH_2)_X CH_3$, $CH=CH_2$, $(CH_2)_X(CF_2)_Y CF_3$, $(CH_2)_X Si(OCH_3)_3$, $(CH_2)_X(N_2C_3H_5)$, and $(CH_2)_X PO_3$, wherein X is from 0 to 15 and wherein Y is from 0 to 5.

6. The method of claim 5, wherein R' comprises $(CH_2)_Z CH_3$, and wherein Z is from 0 to 1.

7. The method of claim 1, wherein the surface reagent comprises one or more materials selected from the group consisting of methyltrimethoxy-silane, and tridecafluorooctyltriethoxy-silane.

8. The method of claim 1, wherein an amount of the surface reagent is between about 0.25% by weight and about 5% by weight relative to the negative electrode active material structures.

9. The method of claim 1, wherein the mixture is operable as an electrolyte, and wherein the mixture comprises an electrolyte salt.

10. The method of claim 1, wherein the mixture comprises water, and wherein the water catalyzes formation of the surface layer.

11. The method of claim 1, further comprising outgassing the mixture comprising the negative electrode active material structures and the surface reagent.

12. The method of claim 1, further comprising heating the mixture to a temperature of at least about 80° C.

13. A method of forming a surface layer on electrode active material structures for a lithium ion battery, the method comprising:
- receiving the electrode active material structures, wherein the electrode active material structures are lithium titanium oxide;
- combining the electrode active material structures with a liquid to form a slurry;
- adding a surface reagent into the slurry, the surface reagent comprising methyltrimethoxy-silane, wherein the methyltrimethoxy-silane covalently bonds with titanium oxides of the lithium titanium oxide in the slurry to form a conformal monolayer surface bonded to the lithium titanium oxide;
- coating the slurry onto a current collecting substrate; and
- drying the slurry on a surface of the current collecting substrate, thereby forming an electrode active material layer,
- wherein the electrode active material structures in the electrode active material layer comprise a surface layer covalently bound to the electrode active material structures, the surface layer formed from the surface reagent, the surface layer reducing reactivity of the electrode active material structures with respect to electrolyte components.

14. A method of forming a surface layer on negative electrode active material structures for a lithium ion battery, the method comprising:
- receiving the negative electrode active material structures, wherein the negative electrode active material structures are lithium titanium oxide;
- combining the negative electrode active material structures with a liquid to form a slurry;
- adding a surface reagent into the slurry, wherein the surface reagent is methyltrimethoxy-silane;
- coating the slurry onto a current collecting substrate wherein the surface reagent reacts with hydroxide groups on the lithium titanium oxide negative electrode active material structures to covalently bond with titanium oxides;
- drying the slurry on a surface of the current collecting substrate, thereby forming an electrode active material layer, wherein the negative electrode active material structures in the electrode active material layer comprise a surface layer containing siloxane, the surface layer covalently bound to the negative electrode active material structures; and
- reducing reactivity of the negative electrode active material structures with respect to electrolyte components through the surface layer containing siloxane.

15. The method of claim 14, further comprising compressing the slurry coating on the current collecting substrate to a density of 1.8 g/cm$^3$ before drying the slurry.

16. The method of claim 13, wherein an amount of the surface reagent may be between 0.5% and 2% by weight relative to the electrode active material structures.

* * * * *